(12) United States Patent
Bracken

(10) Patent No.: US 8,241,253 B2
(45) Date of Patent: Aug. 14, 2012

(54) SECUREMENT SYSTEM FOR A MEDICAL ARTICLE

(75) Inventor: Ronald L. Bracken, Monroe, GA (US)

(73) Assignee: C.R. Bard, Inc., Covington, GA (US)

( * ) Notice: Subject to any disclaimer, the term of this patent is extended or adjusted under 35 U.S.C. 154(b) by 607 days.

(21) Appl. No.: 12/177,092

(22) Filed: Jul. 21, 2008

(65) Prior Publication Data

US 2009/0137961 A1 May 28, 2009

Related U.S. Application Data

(60) Provisional application No. 60/951,059, filed on Jul. 20, 2007.

(51) Int. Cl.
*A61M 5/32* (2006.01)
(52) U.S. Cl. ........................ 604/179; 604/180
(58) Field of Classification Search .................. 604/177, 604/179, 180, 164.04, 174, 523; 602/64
See application file for complete search history.

(56) References Cited

U.S. PATENT DOCUMENTS

| | | | |
|---|---|---|---|
| 2,525,398 A | 10/1950 | Collins | |
| 2,533,961 A | 12/1950 | Rousseau et al. | |
| 2,707,953 A | 5/1955 | Ryan | |
| 3,059,645 A | 10/1962 | Hasbrouck et al. | |
| 3,064,648 A | 11/1962 | Bujan | |
| 3,482,569 A | 12/1969 | Raffaelli | |
| 3,613,663 A | 10/1971 | Johnson | |
| 3,630,195 A | 12/1971 | Santomieri | |
| 3,677,250 A | 7/1972 | Thomas | |
| 3,766,915 A | 10/1973 | Rychlik | |
| 3,834,380 A | 9/1974 | Boyd | |
| 3,856,020 A | 12/1974 | Kovac | |
| 3,906,946 A | 9/1975 | Nordstrom | |
| 3,973,565 A | 8/1976 | Steer | |
| 4,020,835 A | 5/1977 | Nordstrom et al. | |
| 4,057,066 A | 11/1977 | Taylor | |
| 4,059,105 A | 11/1977 | Cutruzzula et al. | |
| 4,129,128 A | 12/1978 | McFarlane | |
| 4,161,177 A | 7/1979 | Fuchs | |
| 4,165,748 A | 8/1979 | Johnson | |
| 4,193,174 A | 3/1980 | Stephens | |
| 4,224,937 A | 9/1980 | Gordon | |
| 4,248,229 A | 2/1981 | Miller | |
| 4,250,880 A | 2/1981 | Gordon | |
| 4,275,721 A | 6/1981 | Olson | |

(Continued)

FOREIGN PATENT DOCUMENTS

EP 0064284 4/1982

(Continued)

*Primary Examiner* — Bhisma Mehta
*Assistant Examiner* — Imani Hayman
(74) *Attorney, Agent, or Firm* — Knobbe Martens Olson & Bear LLP

(57) ABSTRACT

A medical article, such as a catheter, is secured to a patient with a support structure and a plurality of attachment/receiving surfaces that permit the catheter to be reoriented in multiple positions relative to the support structure including rotating the catheter about a longitudinal axis. The support structure may be an anchor pad, strap, or other structure. The plurality of attachment/receiving surfaces may be hook and loop type fasteners that are adhered to the catheter body and to the support structure. The placement of the support structure on the patient is not critical as the catheter position is not fixed relative to the support structure.

28 Claims, 23 Drawing Sheets

U.S. PATENT DOCUMENTS

| | | |
|---|---|---|
| 4,316,461 A | 2/1982 | Marais et al. |
| 4,326,519 A | 4/1982 | D'Alo et al. |
| 4,333,468 A | 6/1982 | Geist |
| 4,362,156 A | 12/1982 | Feller, Jr. et al. |
| 4,392,853 A | 7/1983 | Muto |
| 4,397,647 A | 8/1983 | Gordon |
| 4,449,975 A | 5/1984 | Perry |
| 4,453,933 A | 6/1984 | Speaker |
| 4,480,639 A | 11/1984 | Peterson et al. |
| 4,484,914 A | 11/1984 | Brown |
| 4,534,762 A | 8/1985 | Heyer |
| 4,711,636 A | 12/1987 | Bierman |
| 4,737,143 A | 4/1988 | Russell |
| 4,742,824 A | 5/1988 | Payton et al. |
| 4,808,162 A | 2/1989 | Oliver |
| 4,822,342 A | 4/1989 | Brawner |
| 4,846,807 A | 7/1989 | Safadago |
| 4,852,844 A | 8/1989 | Villaveces |
| 4,857,058 A | 8/1989 | Payton |
| 4,863,432 A | 9/1989 | Kvalo |
| 4,897,082 A | 1/1990 | Erskine |
| 4,898,587 A | 2/1990 | Mera |
| 4,919,654 A | 4/1990 | Kalt |
| 4,921,199 A | 5/1990 | Villaveces |
| 4,955,864 A | 9/1990 | Hajduch |
| 4,976,700 A | 12/1990 | Tollini |
| 5,037,397 A | 8/1991 | Kalt et al. |
| 5,073,170 A | 12/1991 | Schneider |
| 5,084,026 A | 1/1992 | Shapiro |
| 5,098,399 A | 3/1992 | Tollini |
| 5,147,322 A | 9/1992 | Bowen et al. |
| 5,156,641 A | 10/1992 | White |
| 5,192,273 A | 3/1993 | Bierman et al. |
| 5,192,274 A | 3/1993 | Bierman |
| 5,195,981 A | 3/1993 | Johnson |
| 5,236,421 A | 8/1993 | Becher |
| 5,266,401 A | 11/1993 | Tollini |
| 5,292,312 A | 3/1994 | Delk et al. |
| 5,304,146 A | 4/1994 | Johnson et al. |
| 5,306,243 A | 4/1994 | Bonaldo |
| 5,306,256 A | 4/1994 | Jose |
| 5,308,339 A | 5/1994 | Kalt et al. |
| 5,314,411 A | 5/1994 | Bierman |
| 5,338,308 A | 8/1994 | Wilk |
| 5,342,317 A | 8/1994 | Claywell |
| 5,344,406 A | 9/1994 | Spooner |
| 5,354,282 A | 10/1994 | Bierman |
| 5,372,589 A | 12/1994 | Davis |
| 5,380,293 A | 1/1995 | Grant |
| 5,380,395 A | 1/1995 | Uchida |
| 5,403,285 A | 4/1995 | Roberts |
| 5,413,562 A | 5/1995 | Swauger |
| 5,415,642 A | 5/1995 | Shepherd |
| 5,443,460 A | 8/1995 | Miklusek |
| 5,456,671 A | 10/1995 | Bierman |
| 5,468,231 A | 11/1995 | Newman et al. |
| 5,470,321 A | 11/1995 | Forster et al. |
| D364,922 S | 12/1995 | Bierman |
| 5,496,282 A | 3/1996 | Militzer et al. |
| 5,496,283 A | 3/1996 | Alexander |
| 5,499,976 A | 3/1996 | Dalton |
| 5,520,656 A | 5/1996 | Byrd |
| 5,527,293 A | 6/1996 | Zamierowski |
| 5,549,567 A | 8/1996 | Wolman |
| D375,355 S | 11/1996 | Bierman |
| 5,578,013 A | 11/1996 | Bierman |
| 5,593,395 A | 1/1997 | Martz |
| 5,637,098 A | 6/1997 | Bierman |
| 5,653,232 A | 8/1997 | Rogers et al. |
| 5,672,159 A | 9/1997 | Warrick |
| 5,685,859 A | 11/1997 | Komerup |
| 5,693,032 A | 12/1997 | Bierman |
| 5,722,959 A | 3/1998 | Bierman |
| 5,810,781 A | 9/1998 | Bierman |
| 5,833,663 A | 11/1998 | Bierman et al. |
| 5,911,707 A | 6/1999 | Wolvek et al. |
| 6,132,398 A | 10/2000 | Bierman |
| 6,132,399 A | 10/2000 | Shultz |
| 6,213,979 B1 | 4/2001 | Bierman |
| 6,663,582 B2 * | 12/2003 | Ballard et al. .................. 602/64 |
| 2007/0287963 A1 * | 12/2007 | Bierman ....................... 604/174 |

FOREIGN PATENT DOCUMENTS

| | | |
|---|---|---|
| EP | 0247590 | 12/1987 |
| EP | 0356683 | 7/1990 |
| FR | 2381529 | 2/1978 |
| GB | 2063679 A | 6/1981 |
| GB | 2211417 A | 7/1989 |
| WO | WO 92/19309 | 11/1992 |
| WO | WO 97/15342 | 5/1997 |
| WO | WO 98/43691 | 10/1998 |
| WO | WO 99/16327 | 4/1999 |

* cited by examiner

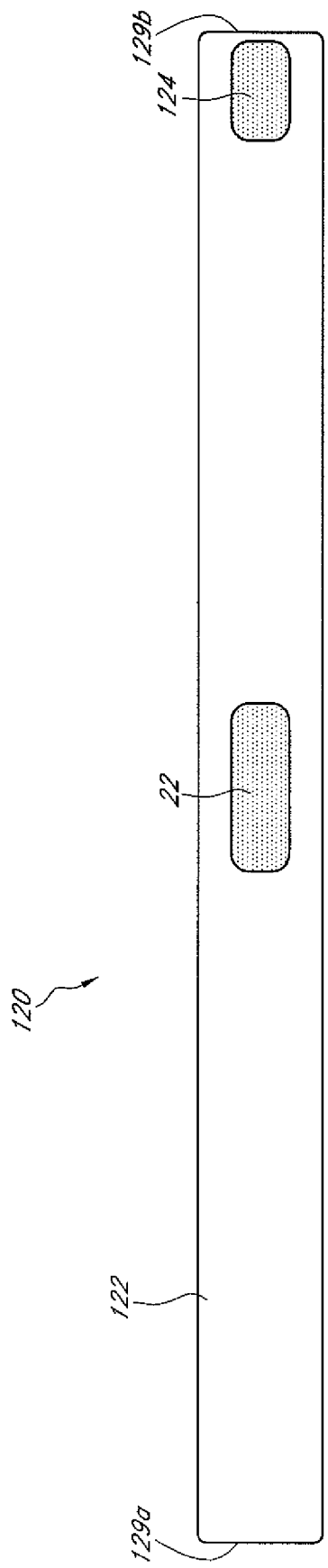
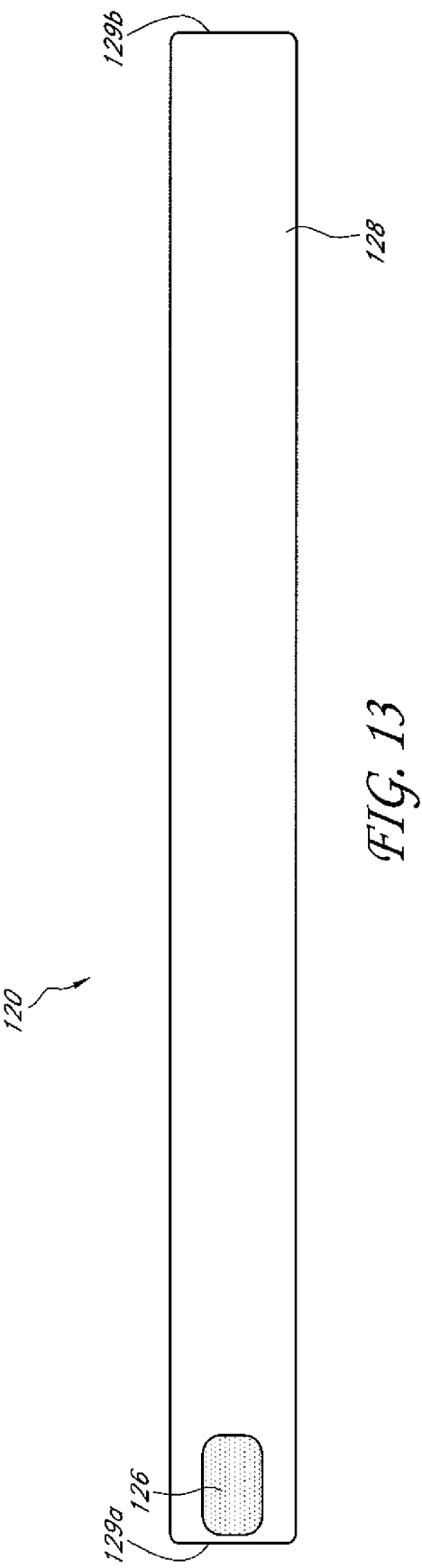

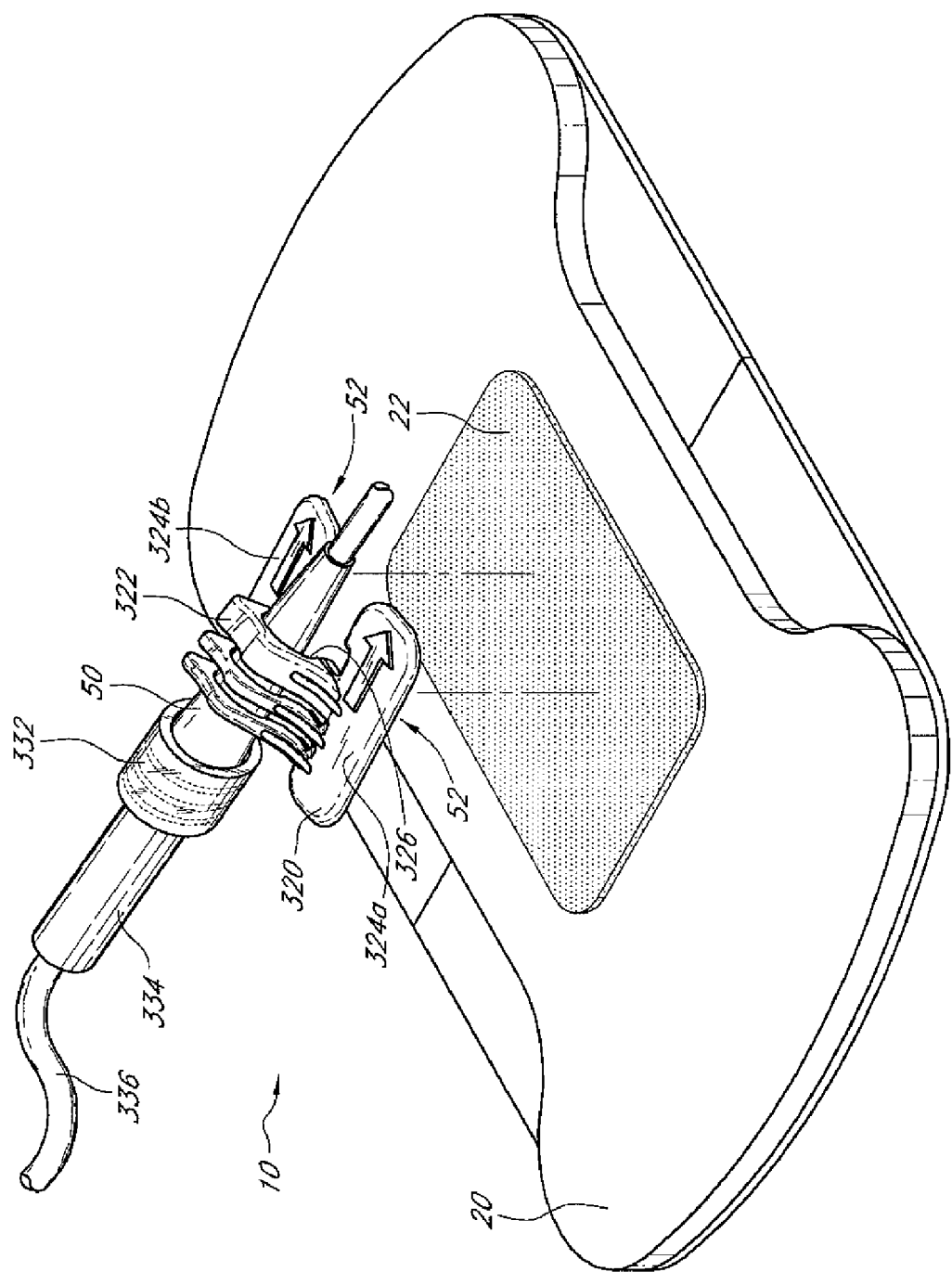

SECUREMENT SYSTEM FOR A MEDICAL ARTICLE

RELATED APPLICATIONS

This application claims the benefit of U.S. Provisional Application No. 60/951,059, filed on Jul. 20, 2007, entitled "CATHETER WITH INTEGRAL SECUREMENT DEVICE," which is hereby incorporated by reference in its entirety.

BACKGROUND

1. Field of the Invention

The present invention relates generally to techniques and systems for securing a catheter or other medical article to a patient.

2. Description of the Related Art

Medical patients are often in need of repetitious administering of fluids or medications, or repetitious draining of fluids. It is very common in the medical industry to utilize medical tubing to provide various liquids or solutions to a patient. For example, medical tubing such as a catheter is often used to introduce fluids and medications directly into the patient or to withdraw fluids from the patient. In many cases, the catheter remains in place for many days. In some instances, a catheter may be attached to a patient for an even lengthier period of time, and may require minimal movement for proper functioning.

It is often advantageous to restrict the movement of the catheter. A moving catheter may cause discomfort to the patient, restrict the administering of fluids or medications or the draining of fluids, cause infection, or become dislodged from the patient unintentionally. In order to keep the catheter or other medical tubing properly positioned for the duration of treatment, the catheter or medical tubing can be secured to the patient in a variety of ways. Most commonly, the medical provider may attempt to restrict movement of the catheter by securing the distal end of the catheter to the patient using tape. Medical providers commonly place long pieces of tape across the distal end of the catheter, often in a crisscross pattern, to secure the catheter distal end to the patient. This securement is intended to inhibit disconnection between the catheter and the patient or between the catheter and another medical article, such as a drainage tube, as well as to prevent the catheter from catching on other objects, such as on a bed rail.

Securing a catheter with tape upon the patient, however, has certain drawbacks. For example, taped connections often collect contaminants and dirt. This potentially can lead to infection of the patient, particularly at an insertion site where the catheter is inserted into the patient. Normal protocol therefore requires periodic tape changes in order to inhibit germ growth.

Periodic tape changes may also be necessary when replacing or repositioning the medical article. The frequent, often daily, removal and reapplication of adhesive tape to the skin of the patient can excoriate the skin. Such repeated applications of tape over the catheter or medical tubing can additionally lead to the build up of adhesive residue on the outer surface of the catheter or medical tubing. This residue can result in contaminants adhering to the catheter itself, increasing the likelihood of infection of the insertion site. This residue can also make the catheter or medical tubing stickier and more difficult to handle for medical providers.

To add to the above problems, valuable time is spent applying and reapplying the tape to secure the catheter. And medical providers often remove their gloves when taping because most find the taping procedure difficult and cumbersome when wearing gloves, especially when the catheter has become sticky from repeated tape applications. Not only does this further lengthen the procedure, but it also may subject the medical provider to possible infection and increase the risk of needle-stick.

Furthermore, tape often fails to limit catheter motion and, therefore, contributes to motion related complications like phlebitis, infiltration and catheter migration. Also, the removal of taped dressings can itself cause undesired motion of the catheter upon the patient. Thus, a patient is subjected to a risk each time that the catheter is intentionally or unintentionally moved or adjusted.

There remains a need for an improved catheter securement system for use with a patient that overcomes the problems associated with current designs. There is a need for a simple, inexpensive connection mechanism that can easily and safely be used to reposition a catheter if desired.

SUMMARY

One aspect of the present invention thus involves a medical article assembly. The assembly includes a medical article that has a medical line and a mounting surface with a first interlocking part. The assembly further includes a support that has two opposed sides. One side is configured for attachment to a patient's skin and the other side has a mounting surface with a second interlocking part for selective engagement with the first interlocking part of the medical article so that the medical article is selectively connected to the support at any orientation and can be disconnected and repositioned at any orientation.

Another aspect involves a device for securing an intravenous medical article inserted into a body portion of a patient. The device includes a flexible anchor pad having two opposed surfaces and a biocompatible adhesive layer disposed on one of the opposed surfaces of the flexible anchor pad with a release sheet removably disposed over the adhesive layer. The device further includes a hook and loop fastener that has a hook portion and a loop portion releasably connected to each other and disposed on the other one of the opposed surfaces of the flexible anchor pad. The device further includes an adhesive layer disposed on at least a portion of the hook and loop fastener for connection to a medical article. The medical article has a body directly mounted to the adhesive layer on the hook and loop fastener, such that when the anchor pad is secured to a patient's skin, the medical article can be reoriented at a plurality of directions with respect to the anchor pad by removing and reattaching one portion of the hook and loop fastener to the other portion.

Yet another aspect involves a method of securing a medical article to a medical patient. The method includes providing a medical article having a mounting portion and a hook and loop fastener. The hook and loop fastener includes a first part fixed to the mounting portion of the medical article and a second part for attachment to the patient. The method further includes securing the second part of the hook and loop fastener to the patient and selectively positioning the catheter with respect to the patient by unfastening the first part of the hook and loop fastener from the second part of the hook and loop fastener, orienting the medical article at any desired position in a plane generally parallel to the surface of the skin of the patient, and reconnecting the first part of the hook and loop fastener to the second part of the hook and loop fastener to secure the medical article to the patient.

Yet another aspect involves a securement system for securing a medical article to a patient. The system includes a medical article that has a plurality of attachment surfaces and a support structure configured to attach to the patient and having a plurality of receiving areas at which the plurality of attachment surfaces are configured to engage so as to inhibit movement of the medical article with respect to the support structure in at least one direction.

Yet another aspect involves a device for securing a medical article inserted into a body portion of a patient that comprises a flexible anchor pad having a first attachment surface on a first side and an adhesive surface on a second side, the adhesive being biocompatible and a medical article having a second attachment surface such that when the anchor pad is secured to a patient's skin, the medical article can be reoriented at any direction with respect to the anchor pad by removing and reattaching the second attachment surface from the first attachment surface.

Further aspects, features and advantages of the present invention will become apparent from the detailed description of certain embodiments that follows.

BRIEF DESCRIPTION OF THE DRAWINGS

The above mentioned and other features of the invention will now be described with reference to the drawings of several embodiments of the present securement system. The illustrated embodiments of the securement system are intended to illustrate, but not to limit the invention. The drawings contain the following figures:

FIG. 12 is a top view of the strap from FIG. 11.

FIG. 13 is a bottom view of the strap from FIG. 12.

FIG. 32 is a perspective view of a securement system in accordance with another embodiment of the present invention and shows an anchor pad, a retainer, and a catheter hub secured by the retainer, prior to the securement of the retainer onto the anchor pad.

DETAILED DESCRIPTION OF CERTAIN EMBODIMENTS

Figure 1:
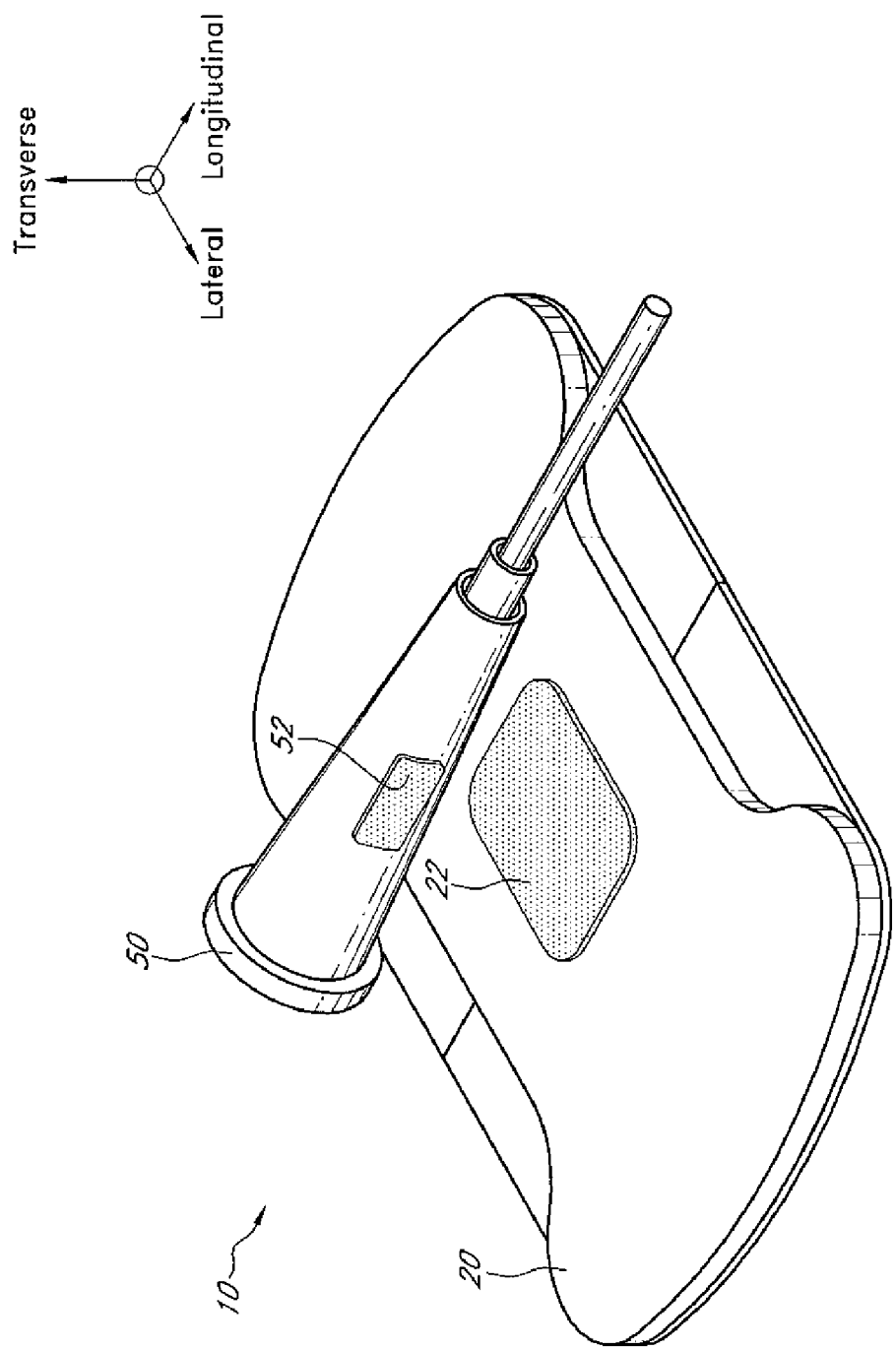
FIG. 1 is a perspective view of a securement system in accordance with a preferred embodiment of the present invention and shows a catheter hub and anchor pad prior to the securement of the catheter hub onto the anchor pad.

The following description and examples illustrate preferred embodiments of the present securement system disclosed in the context of use with an exemplary catheter hub. More specifically, the embodiments relate to a securement system and related techniques that maintain a medical article in position upon a patient. The embodiments of the securement system are illustrated with a catheter adapter or hub. The principles of the present invention, however, are not limited to catheter adapters or hubs such as those shown. It will be understood by those of skill in the art in view of the present disclosure that the securement system described can be used with other types of medical articles, including, but not limited to catheters of various design, either with or without connectors, such as central venous catheters, peripherally inserted central catheters, hemodialysis catheters, Foley catheters, as well as other designs of catheter hubs and catheter adaptors. Other medical articles may include surgical drainage tubes, feeding tubes, chest tubes, nasogastric tubes, rectal drains, external ventricular drains, chest tubes, any other sort of fluid supply or medical lines, connector fittings, and scopes, as well as electrical wires or cables connected to external or implanted electronic devices or sensors. The medical articles can be a single medical article or a combination of medical articles.

One skilled in the art may also find additional applications for the devices and systems disclosed herein. Accordingly, the illustration and description of the securement system in connection with a catheter hub is merely exemplary of one possible application of the securement system and technique disclosed. For case of description, the term catheter is used herein to generically refer to the above listed medical articles, for example but without limitation, and should not be construed in a limited manner.

The securement system described herein is especially adapted to arrest transverse, lateral, and/or longitudinal movement of a catheter, as well as hold the catheter against the patient. The securement system accomplishes this without meaningfully impairing (i.e., substantially occluding) fluid flow through the medical catheter. As described below, retention mechanisms to accomplish this include, among others, attachment surfaces located on the catheter and on an anchor pad or strap for attachment to the patient.

The securement system releasably engages the catheter. This allows the catheter to be disconnected from the anchor pad or strap, and from the patient, for any of a variety of known purposes. For instance, the medical provider may want to remove the catheter from the anchor pad to ease disconnection of a medical article from the catheter or to clean the patient. The disengagement of the catheter from the anchor pad, however, can be accomplished without removing the anchor pad from the patient. Thus, the medical provider may move the catheter without irritating the skin of the patient. In addition, the medical provider may, using some embodiments, adjust the position of the catheter without disengaging the catheter from the anchor pad or strap.

No part of the anchoring system is destroyed during disengagement of the securement system. In this way, the components of the securement system can be reused. It is not limited to use for only one catheter, but can be used multiple times for the same catheter or for different catheters, at the same or different times. After disengagement of the catheter, the anchor pad or strap is ready for re-engaging with the same or a different catheter. Similarly, the catheter may thereafter re-engage with the same or a different anchor pad. A detailed description of embodiments of a securement system, and its associated method of use, now follows.

With reference now to FIG. 1, an embodiment of a securement system 10 includes an anchor pad 20 and a medical article 50 in the form of a catheter hub. The anchor pad 20 is configured to be secured to a patient's skin. The catheter 50 is configured to attach to the anchor pad 20 by engaging two or more attachment surfaces 22 and 52.

To assist in the description of the components of embodiments of the anchoring system, the following coordinate terms are used, consistent with the coordinate axes illustrated in FIG. 1. A "longitudinal axis" is generally parallel to a section of a medical article retained by the securement system 10. A "lateral axis" is normal to the longitudinal axis and is generally parallel to the plane of the anchor pad 20. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The terms "proximal" and "distal" are used in reference to the center of the patient's body.

Figure 2:
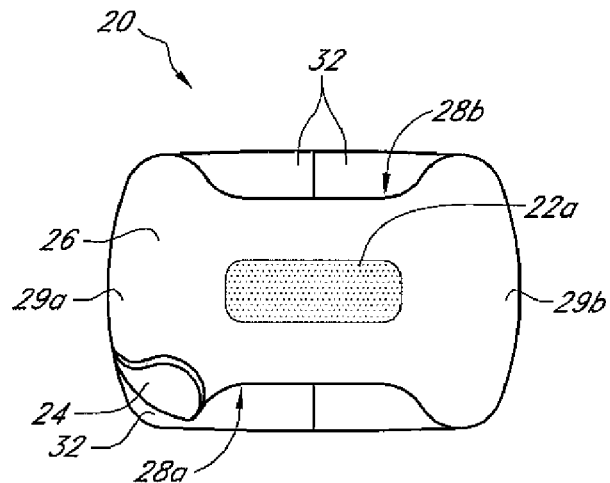
FIG. 2 is a top view of the anchor pad from FIG. 1 with a rectangular attachment surface.

FIG. 2 illustrates the anchor pad 20. The anchor pad 20 has a lower adhesive surface 24 which may adhere to the skin of a patient and an upper layer 26. The upper layer 26 comprises one or more receiving or attachment surfaces 22a, 22b, 22c for receiving an attachment surface 52 of the medical article. The one or more attachment surfaces 22 may be disposed on an upper surface of the upper layer 26 or completely or partially inset into the upper layer 26. The one or more attachment surfaces 22 may be recessed into the upper layer 26 so as to form a well or receptacle. A first attachment surface 22 may be disposed at a different transverse height relative to a second attachment surface of the anchor pad 20.

The attachment surface 22 is configured to receive or engage the attachment surface 52, illustrated in FIG. 1 and disposed on the catheter 50. In the illustrated embodiment, the attachment surface 22 comprises hook fasteners configured to interact with loop fasteners disposed on the attachment surface 52. These types of fastening mechanisms provide a secure interlock between the attachment surface 22 and the attachment surface 52, but may be detached and reattached in any desired orientation. Of course, the hook fasteners on the attachment surface 22 and the loop fasteners on the attachment surface 52 are interchangeable, and loop fasteners may instead by disposed on the attachment surface 22 while hook fasteners are disposed on the attachment surface 52.

The attachment member or surface 22 may comprise any fastener configured to releasably attach to the attachment member or surface 52. For example, the attachment surface 22 may comprise a releasable adhesive. Other fastener mechanisms suitable for use may be configured such that the attachment surface 22 may engage the attachment surface 52 at different orientations. Other suitable interlocking fasteners may comprise features such as a snap-fit, a ball and socket, twist ties, hooks, or friction fittings. Although multiple embodiments of varied size and shape of both the attachment surface 22 and the attachment surface 52 will be described herein, every size and shape of the attachment surface 22 disclosed herein may engage every size and shape of the attachment surface 52 disclosed herein.

For ease of explanation, like reference numerals are used throughout the figures to indicate like features. Individual letters are added as a suffix to the reference numerals when describing individual or varying embodiments of the features. Thus, attachment surfaces 22a, 22b, 22c, etc., described below, are like features as described in reference to the attachment surface 22, but may be embodied in different configurations, such as characterized by a different shape.

Attachment surface 22a in FIG. 2 is illustrated as a having a substantially rectangular shape with rounded corners. The size and shape of the attachment surface 22a is configured such that the attachment surface 52 on the catheter 50 may engage the attachment surface 22a at a variety of lateral and longitudinal locations. In addition, the size and shape of the attachment surface 22a enable the attachment surface 52 to be rotated in any direction in the place of the anchor pad 20 and still engage the attachment surface 22a.

In the illustrated embodiment, the attachment surface 22a is substantially centered on the upper layer 26. Such placement of the attachment surface 22a increases the likelihood that a force applied to the attachment surface 22a will be dispersed equally about the anchor pad 20 and that the anchor pad 20 will maintain a secure connection to the patient. The attachment surface 22a may, however, be placed anywhere on the upper layer 26. In some embodiments, the attachment surface 22a is offset on the upper layer 26 to allow for specific placement on a patient's skin. For example, the attachment surface 22a may be disposed at one end of the upper layer 26. This end may be attached to upper portion of the wrist of the patient, while the remaining portion of the anchor pad 20 is wrapped about the wrist.

The attachment surface 22 may be mounted on the upper layer 26 in any number of ways. For example, the attachment surface 22 may be mounted to the upper layer 26 by a layer of adhesive, such as pressure sensitive adhesive or hot glue. Other possible adhesives include a solvent bond adhesive, such as cyanoacrylate or other bonding material. Any suitable adhesive may be used to obtain a secure connection that will resist disconnection of the attachment surface 22 from the upper layer 26 when the attachment surface 22 is disengaged from the attachment surface 52. In some embodiments, the attachment surface 22 may not be mounted to the upper layer 26, but rather may be integral to the upper layer 26.

In combination, the lower adhesive surface 24, upper layer 26, and possibly one or more intermediate layers may comprise a laminate structure. A suitable laminate that comprises a foam or woven material with an adhesive layer is available commercially from Avery Dennison of Painsville, Ohio. The anchor pad 20 may be configured as a flexible structure configured to conform to the surface of a patient's skin.

The lower adhesive surface or layer 24 may be a medical-grade adhesive and can be either diaphoretic or nondiaphoretic, depending upon the particular application. The lower adhesive surface 24 may have additional types of medical adhesives laminated thereto. The adhesive surface 24 may be a solid layer or may be configured as an intermittent layer such as in a pattern of spots or strips. Although not illustrated, it will be understood that the anchor pad 20 can include suture holes in addition to the adhesive layer to further secure the anchor pad 20 to the patient's skin.

The lower adhesive surface 24 can be applied to the anchor pad 20 during manufacture and may be further covered with a release liner 32, described below. Alternatively, it is possible to apply a double-sided adhesive tape to the upper layer 26 before application.

The upper layer 26 may comprise a foam (e.g., closed-cell polyethylene foam) or woven material (e.g., tricot) layer. A surface of the foam or woven material layer constitutes the upper layer 26 of the anchor pad 20. In the alternative, the upper layer 26 may comprise an upper paper or other non-woven cloth layer, and an inner foam layer may be placed between the upper layer 26 and lower adhesive surface 24.

In the illustrated embodiment, the lower adhesive layer 24 and the upper layer 26 have concave sections 28a and 28b that narrow the center of anchor pad 20 where the attachment surface 22 is attached. As a result, the lateral sides of anchor pad 20, illustrated as sections 28a and 28b, have more contact area which provides greater stability and adhesion to a patient's skin. Additionally, a medical article may be inserted into the patient's skin at a location nearer to the attachment surface 22 than if the concave sections 28a and 28b were omitted. The anchor pad 20, however, is not limited to requiring the concave sections 28a and 28b, as in the illustrated embodiment.

A removable release liner 32 may cover the lower adhesive surface 24 before use. The release liner 32 may resist tearing and be divided into a plurality of pieces to assist removal of the release liner 32 and ease attachment of the anchor pad 20 to a patient's skin. In the illustrated embodiment, the release liner 32 is divided in to two adjacent pieces. In addition, the release liner 32 is sized similarly to the upper layer 26, but does not include the concave sections 28a and 28b. Thus, edges of the release liner 32 are exposed beyond the concave sections 28a and 28b and provide a grasping edge for easy removal of the release liner 32. The liner may be made of a paper, plastic, polyester, or similar material. For example, the release liner 32 may comprise a material made of polycoated, siliconized paper, or another suitable material such as high density polyethylene, polypropylene, polyolefin, or silicon coated paper.

The anchor pad 20 may have any shape that allows attachment of the anchor pad 20 to a patient's skin and allows the attachment surface 22 to be mounted on the upper layer 26. The anchor pad 20 may be oval, polygonal or round, for example. As can be seen in FIG. 2, the upper layer 26 is roughly rectangularly shaped with rounded ends and concave sections 28a and 28b. The concave sections 28a and 28b provide access to the release liner 32 for easier removal of the release liner 32 and easier application of the anchor pad 20. The anchor pad 20 is not limited to the illustrated shape, however, and the release liner 32 may have a shape commensurate with that of the lower adhesive layer 24 and the upper layer 26.

Figure 3:
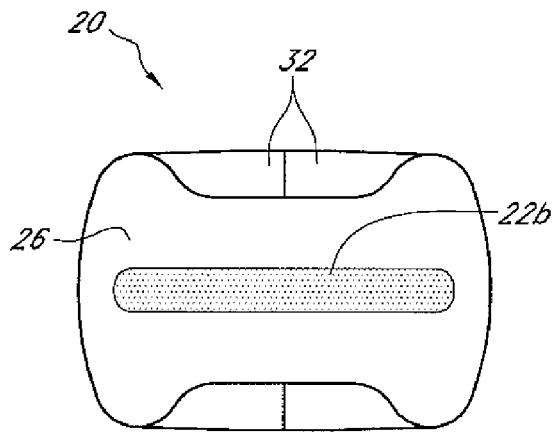
FIG. 3 is a top view of another embodiment of the anchor pad from FIG. 2 with a different shaped attachment surface than the attachment surface in FIG. 2.

FIG. 3 illustrates another embodiment of the anchor pad 20. The attachment surface 22 is illustrated as having a different shape in FIG. 3 than the attachment surface 22a illustrated in FIG. 2. Attachment surface 22b is mounted on the upper layer 26.

The attachment surface 22b is shaped as an elongated strip. In the illustrated embodiment, the attachment surface 22b is longer than the attachment surface 22a, but the attachment surface 22b is not as wide as the attachment surface 22a. Thus, the attachment surface 22b provides a greater lateral area along which to attach the catheter 50. The attachment surface 22b, however, reduces the longitudinal area along which the catheter 50 may be attached. Thus, this embodiment of the anchor pad 20 may be useful when a greater lateral leeway is desired, while still providing a targeted attachment area. The attachment surface 22b may otherwise be configured similar to the attachment surface 22a.

Figure 4:
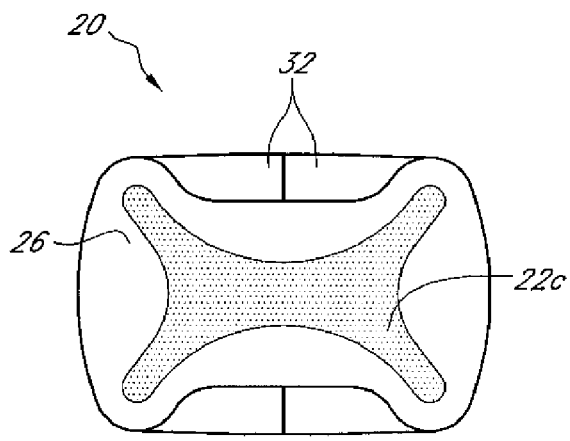
FIG. 4 is a top view of another embodiment of the anchor pad from FIG. 2 with a generally star-shaped attachment surface.

FIG. 4 illustrates another embodiment of the anchor pad 20 where the attachment surface 22 is illustrated as having a different shape than the attachment surface 22a illustrated in FIG. 2. In FIG. 4, attachment surface 22c is illustrated as having a curvilinear shape, generally forming a curved "X" pattern or a butterfly shape. This shape allows the catheter 50 to be attached along the majority of the anchor pad 20, including to areas near the corners of the anchor pad 20. Forming the attachment surface 22c in the curved shape as illustrated in FIG. 4, however, provides ample surface area for the upper layer 26 and the lower adhesive layer 24 to securely attach the anchor pad 20 to the patient and resist detachment from the patient when a force pulls the attachment surface 22c away from the upper layer 26. The attachment surface 22c may otherwise be configured similar to the above described attachment surfaces.

The attachment surface 22 may be shaped differently, disposed on a different area of the upper layer 26, or otherwise configured different from the attachment surfaces 22a-22c. Different shapes provide varied locations for positioning the catheter 50. A larger or more complex shaped attachment surface 22 may allow the placement of the anchor pad 20 and/or the catheter 50 on the anchor pad 20 to be less precise. This lenient requisite precision may contribute to easier application by a medical provider. Various shapes, sizes and configurations of the attachment surface 22 may be used depending on the desired application.

The attachment surface 22 may be configured in any way that allows engagement with the attachment surface 52. For example, multiple attachment surfaces 22 may be disposed on the anchor pad 20, as will be described later. In addition, the attachment surface 22 may cover the majority or substantially the entire upper layer 26. In some embodiments, the attachment surface 22 is integral to the upper layer 26. The attachment surfaces 22a-22c are illustrative embodiments of the attachment surface 22 only and are not limiting in any way.

Figure 5:
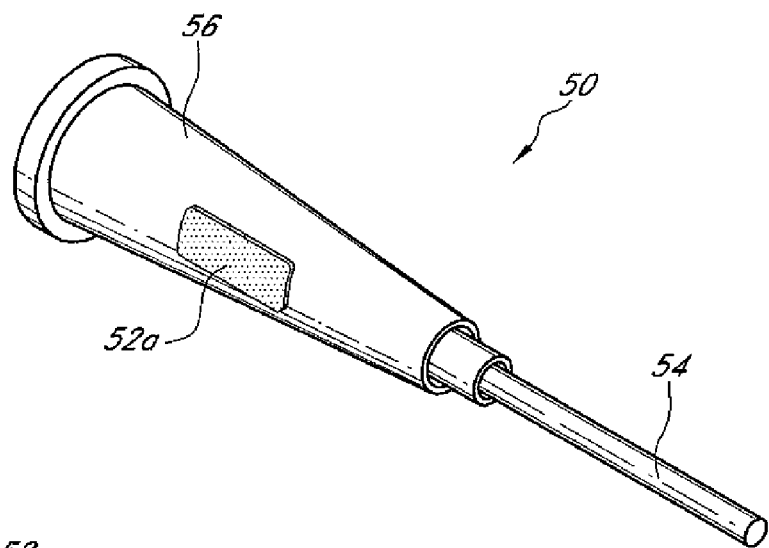
FIG. 5 is a perspective view of the catheter hub from FIG. 1 and shows an attachment surface configured to secure to any of the attachment surfaces illustrated in FIG. 2-4.

FIG. 5 illustrates an exemplary medical article for use with the embodiments of the securement device described herein. The medical article can be a single medical article or a combination of one or more medical articles. Such medical articles can be or include, for example, but without limitation, connector fittings, catheters, catheter hubs, catheter adaptors, fluid supply lines, or other similar articles. FIG. 5 is a perspective view of a catheter hub 50. The catheter hub 50 may be connected to a connector fitting. The connector fitting is preferably disposed upon the end of a medical line which can be connected to a drip bag, blood monitor, or other fluid related medical apparatus. While the anchor pad 20 of FIG. 2 is configured to receive a portion of the catheter hub 50, the anchor pad 20 can be configured for use with the connector fitting.

The catheter hub 50 includes a body that, in the illustrated embodiment, is configured as a catheter hub and has a generally conical shape and tapers from a large radius to a smaller radius along its length. In the illustrated embodiment, the catheter hub 50 does not comprise a laterally extending tab or wings. Of course the catheter hub 50 is not limited to the illustrated structure and may include tabs or wings.

The catheter 50 includes one or more attachment surfaces 52a, and a flexible medical line 54 coupled to a rigid body 56 that may be connected to another medical article to communicate fluids. The catheter hub 50 also can include an external screw thread on the outside of the conical body 56 near the end with the larger radius. The screw thread can be used in association with a spin nut of the connector fitting in order to securely interconnect the connector fitting and the catheter hub 56. The attachment surface 52 is mounted to an outer surface of the rigid body 56.

The catheter 50 may be formed of a medically compatible material, such as a non-allergenic polymer. Other materials may also be used.

As described above, this embodiment of the catheter hub 50 is not limiting and other catheter hubs or medical articles may be used in the securement system 10. For example, catheter 50 can be in the form of any type of medical article that is typically secured to a patient.

The attachment surface 52 is configured to engage, or interlock with, the attachment surface 22 on the anchor pad 20. In the illustrated embodiment, the attachment surface 52 comprises loop fasteners. Of course, the attachment surface 52 may comprise hook fasteners and the attachment surface 22 may comprise a loop fasteners. In some embodiments, the attachment surface 52 comprises other fasteners that engage with the attachment surface 52, as described above in reference to the attachment surface 22.

The attachment surface 52 has a size and shape that facilitates mounting to the body 56. Otherwise, the attachment surface 52 may be configured similar to the attachment surface 22. For example, the attachment surface 52 may be mounted on the body 56 of the catheter 50 similar to the manner in which the attachment surface 22 is mounted to the anchor pad 20. Of course, the attachment surface 52 may vary from the attachment surface 22, such as in the size and shape of the attachment surface 52.

Attachment surface 52a is illustrated in FIG. 5 as having a substantially rectangular shape. The attachment surface 52a is smaller than the attachment surface 22a of the anchor pad 20, illustrated in FIG. 2. Thus, the attachment surface 52a may engage the attachment surface 22a at a plurality of locations, and the attachment surface 52a may be shifted relative to the attachment surface 22a.

The attachment surface 52a and the attachment surface 22a may instead be similar in size and/or shape. In such an embodiment, the attachment surface 52a could be rotated in the plane of the anchor pad 20 and still engage the attachment surface 22, but the ability to engage the attachment surface 52a with the attachment surface 22a at a plurality of lateral and longitudinal locations would be diminished.

In the illustrated embodiment, the attachment surface 52a is substantially longitudinally centered along the body 56. This placement of the attachment surface 52a may increase the likelihood that the catheter 50 securely attaches to the anchor pad 20 when the attachment surface 52a and the attachment surface 22a are engaged. The attachment surface 52a may, however, be longitudinally disposed anywhere along the catheter 50, including on various areas on the body 56 or the flexible medical line 54. The location may be selected according to an intended application or according to the medical article being secured, among other reasons. In some embodiments, the attachment surface 52a is disposed over substantially the entire length of the body 56.

Figure 6:
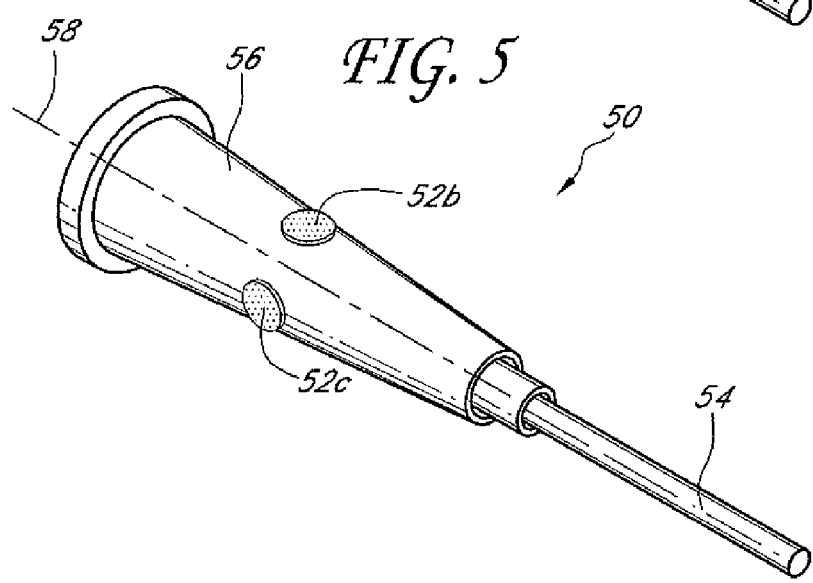
FIG. 6 is a perspective view of another embodiment of the catheter hub from FIG. 5 with a plurality of round attachment surfaces.

FIG. 6 illustrates another embodiment of the catheter 50. The attachment surface 52 is illustrated as a plurality of attachment surfaces 52b and 52c, each having a substantially circular shape. Both of the attachment surfaces 52b and 52c are mounted on the body 56.

The attachment surfaces 52b and 52c are circumferentially disposed around the catheter 50. Thus, the catheter 50 may engage the attachment surface 22 in a plurality of configurations rotated about a longitudinal axis 58 of the catheter 50. The amount of rotation required to shift between attaching the catheter at the attachment surface 52b and attaching the catheter 50 at the attachment surface 52c can be selected as any angle. For example, the attachment surfaces 52b and 52c may be disposed 45° apart, 90° apart, 180° apart, 360° apart, or anywhere between these angles. The angle separated the attachment surfaces 52b and 52c may be selected according to an intended application or according to the medical article being secured, among other reasons.

Two discrete attachment surfaces 52b and 52c are illustrated in FIG. 6. There may, however, be any number of attachment surfaces disposed around the catheter 50. For example, six or eight attachment surfaces may be disposed on the catheter 50.

Longitudinally spaced attachment surfaces may be configured in any number of ways. For example, the attachment surfaces 52b and 52c may be similarly shaped or may have differing shapes. In addition, the attachment surfaces 52b and 52c may be spaced in a configuration defining a circle, or may be spaced at random or according to another pattern such that some attachment surfaces are located at a different axial location along the catheter 50.

Figure 7:
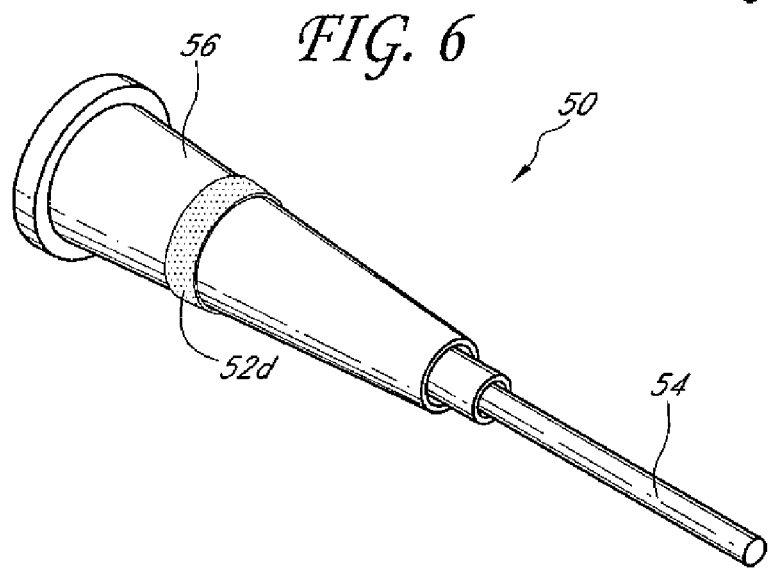
FIG. 7 is a perspective view of another embodiment of the catheter hub from FIG. 5 with an annular shaped attachment surface.

FIG. 7 illustrates another embodiment of the catheter 50 and shows an attachment surface 52d having a different shape than the attachment surface 52a illustrated in FIG. 6. The attachment surface 52d comprises an annular ring circumscribing the catheter 50. Thus, the attachment surface 52d may be formed of a strip that wraps around the catheter 50. This configuration allows the catheter 50 to be rotated about the longitudinal axis 58 into any desired position. Therefore, a medical provider may merely press the catheter 50 into position upon the attachment surface 22 without precisely placing one side of the catheter 50 against the attachment surface 22.

The attachment surface 52d may extend for any width along the catheter 50. A thinner attachment surface 52d will require more precise placement. A thicker attachment surface 52d may allow a more lax placement and may provide more contact area with which to engage the attachment surface 22. In addition, the edges of the attachment surface may be substantially parallel, or they may be angled or curved in relation to themselves and each other.

The attachment surface 52 may be shaped differently, disposed on a different area of the catheter 50, or otherwise configured different from the attachment surfaces 52a-52d. Different shapes provide varied locations for positioning the catheter 50. A larger or more complex-shaped attachment surface 52 may allow the placement of the catheter 50 on the anchor pad 20 to be less precise. Various shapes, sizes and configurations of the attachment surface 52 may be used depending on the desired application.

The attachment surface 52 may be configured in any way that allows engagement with the attachment surface 22. For example, the attachment surface 52 may comprise a plurality of attachment surfaces shaped as dots, squares, strips, or any other shapes. In addition, the attachment surface 52 may cover the majority or substantially the entire surface of the catheter 50 or the body 56. Attachment surfaces may be disposed at a plurality of locations on the catheter 50, being either circumferentially spaced and/or axially spaced, as described below. The attachment surfaces 52a-52d are illustrative embodiments of the attachment surface 52 only and are not limiting in any way.

To use the securement system 10, the anchor pad 20 is attached to a patient. The anchor pad 20 may be attached before or after connected the catheter 20 to the patient and/or to the anchor pad 20. For example, when the medical article 50 is an IV catheter, the healthcare provider may begin by inserting a portion of the catheter 50 into the patient's vein, as is known in the art. Then, the medical provider can attach an intravenous line to the catheter 50 using a luer connection, for example. In this case, the medical provider inserts the tapered or luer end of the connector fitting into the catheter hub and turns a spin nut to thread the spin nut over a threaded flange disposed at the distal end of the hub. This action draws the catheter hub 50 together with the intravenous line and the luer connector and releasably interlocks them. The immediate connection of the intravenous line to the catheter hub 50 inhibits a back flow of blood.

The medical provider may now secure the anchor pad 20 at an appropriate position upon the patient based on the location of the catheter 50 after it has been administered to the patient. To secure the anchor pad 20, the medical provider presses the lower adhesive layer 24 into contact with the patient's skin.

Figure 8:
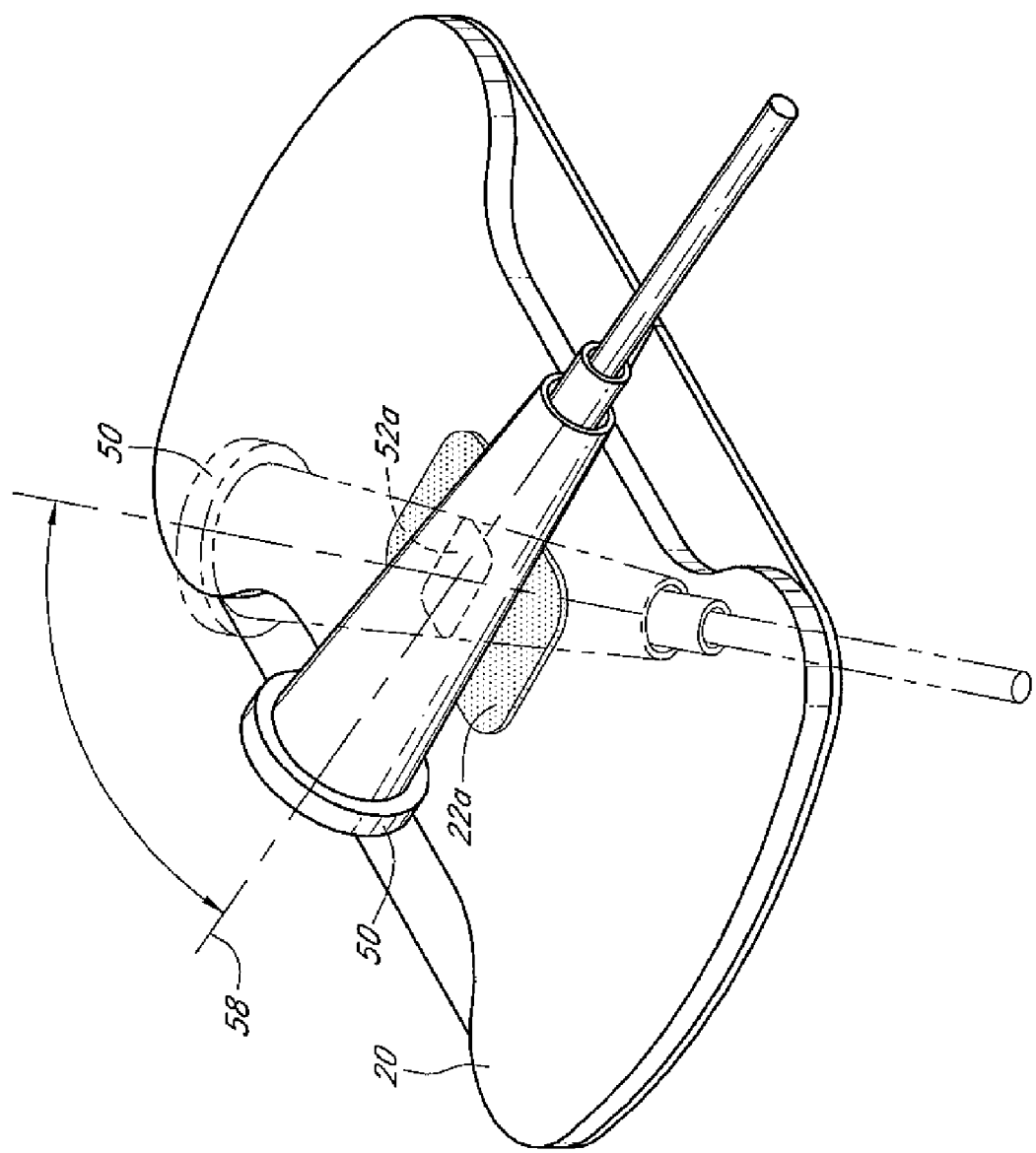
FIG. 8 is a perspective view of the securement system from FIG. 1 with the catheter hub secured to the anchor pad in a plurality of positions.

The release liner 32, however, may first have to be removed. Thereafter, the medical provider secures the catheter 50 in place on the patient by engaging the attachment surface 22 with the attachment surface 52, as shown in FIG. 8. This may be accomplished by pressing the attachment surface 52 against the attachment surface 22 with sufficient force, as is shown in a side view of the securement system 10 in FIG. 9.

The medical provider may, however, choose to attach the anchor pad 20 to the patient before administering the catheter 50. The shapes and sizes of the attachment surfaces 22 and 52 may be determinative of how precisely the medical provider must estimate the ultimate placement of the catheter 50. Larger attachment surfaces 22 and 52 will allow leeway for the medical provider to estimate where the catheter 50 will eventually be attached to the patient. After attaching the anchor pad 20 and then administering the catheter 50, the medical provider may engage, disengage, re-engage . . . the attachment surface 52 with the attachment surface 22.

The securement system 10 can be provided in an assembled condition to prevent loss of parts and to assist the medical provider in administering the catheter 50 quickly. In such situation, the position of the securement system 10 may first be determined. Then, the release liner 32 is removed if necessary, and the securement system 10 is pressed against the patient's skin to secure the lower adhesive layer 24 of the anchor pad 20 to the surface of the skin. At this time, the catheter 50 is already connected to the anchor pad 20. If the catheter 50 has been previously administered to the patient by the medical provider, then the process is complete. If adjustments of the catheter 50 are necessary, such as to improve the functioning of the catheter 50 or to increase the comfort of the patient, then the medical provider may disengage the attachment surface 52 from the attachment surface 22 and subsequently reattach the catheter 50 to the anchor pad 20 in a more appropriate position.

If the catheter 50 has not already been administered to the patient before the securement system 10 is attached to the patient, the catheter 50 can be attached to a medical article or further administered to the patient. The medical provider may do this while the catheter 50 is still attached to the anchor pad 20, or the medical provider may first detach the catheter 50 from the anchor pad 20. Following administration of the catheter 50, the catheter 50 can be precisely positioned or repositioned by disconnecting the attachment surfaces 22 and 52, leaving the anchor pad 20 in position on the patient's skin. The catheter 50 may be oriented in any desired orientation and then reconnected to the anchor pad 20 by pressing the attachment surface 52 against the attachment surface 22.

To disconnect the catheter 50 from the anchor pad 20, a medical provider may pull the catheter 50 away from the anchor pad 20 with a sufficient amount of force. When the catheter 50 is connected to the anchor pad 20, the catheter 50 will be inhibited from moving in one or more directions. The catheter 50 may therefore be inhibited from moving in any or all of a longitudinal, lateral, and transverse direction until sufficient force is applied to the catheter 50 or the anchor pad 20 to disengage the attachment surface 22 and the attachment surface 52.

As can be seen in FIG. 8, the catheter 50 may be repositioned with respect to the anchor pad 20. In the embodiment illustrated in FIG. 8, in which the anchor pad 20 includes the attachment surface 22a and the catheter 50 includes the attachment surface 52a, the catheter 50 may be rotated at any angle in the plane of the anchor pad 20. The catheter 50, illustrated with solid lines, can be rotated to a new position represented by dashed lines. This rotation is demonstrated by the illustrated arrow. Thereafter, the longitudinal axis 58 will be pointed in a different direction and the catheter 50 will be angled different from before.

In addition to being able to rotate within the plane of the anchor pad 20, the catheter 50 may be laterally or longitudinally shifted in relation to the anchor pad 20. As described above, the catheter 50 may be moved forward, back, or side to side along the anchor pad 20 so long as the attachment surface 22 is in a position to engage with the attachment surface 52. The lateral or longitudinal motion may be combined with the rotation described above. Thus, the attachment surface 52 may be received at a plurality of areas on the attachment surface 22.

Figure 9:
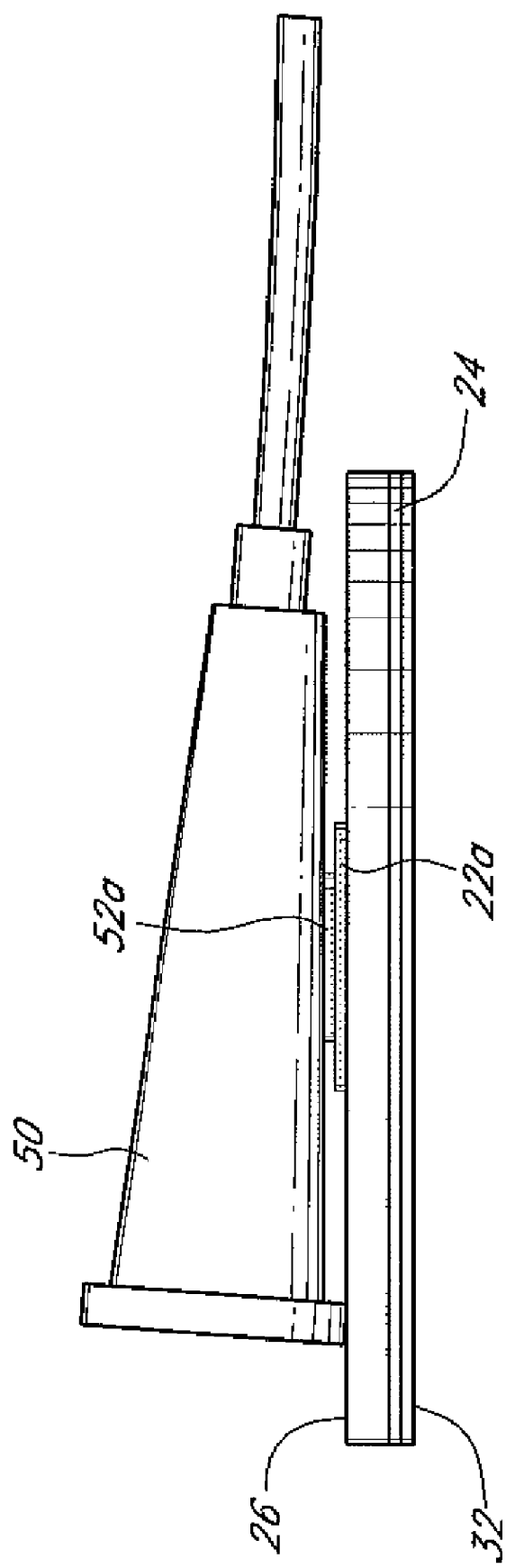
FIG. 9 is a side view of the securement system of FIG. 8 and shows the attachment surface of the catheter hub attached to the attachment surface of the anchor pad.

In FIG. 9, the catheter 50 is moved both laterally—to the right in the figure—and rotated around the longitudinal axis 58. In the illustrated embodiment in which the anchor pad 20 includes the attachment surface 22a and the catheter 50 includes the attachment surface 52a, the catheter 50 may be rotated by any amount around the axis 58. Thus, a medical provider may rotate the catheter 50 by 23°, 58°, 83°, 122°, 159°, 202°, 248°, 277°, 315°, 360°, or anywhere inbetween. Depending on the configuration of the attachment surface 22, the catheter 50 may also be moved longitudinally.

Figure 10:
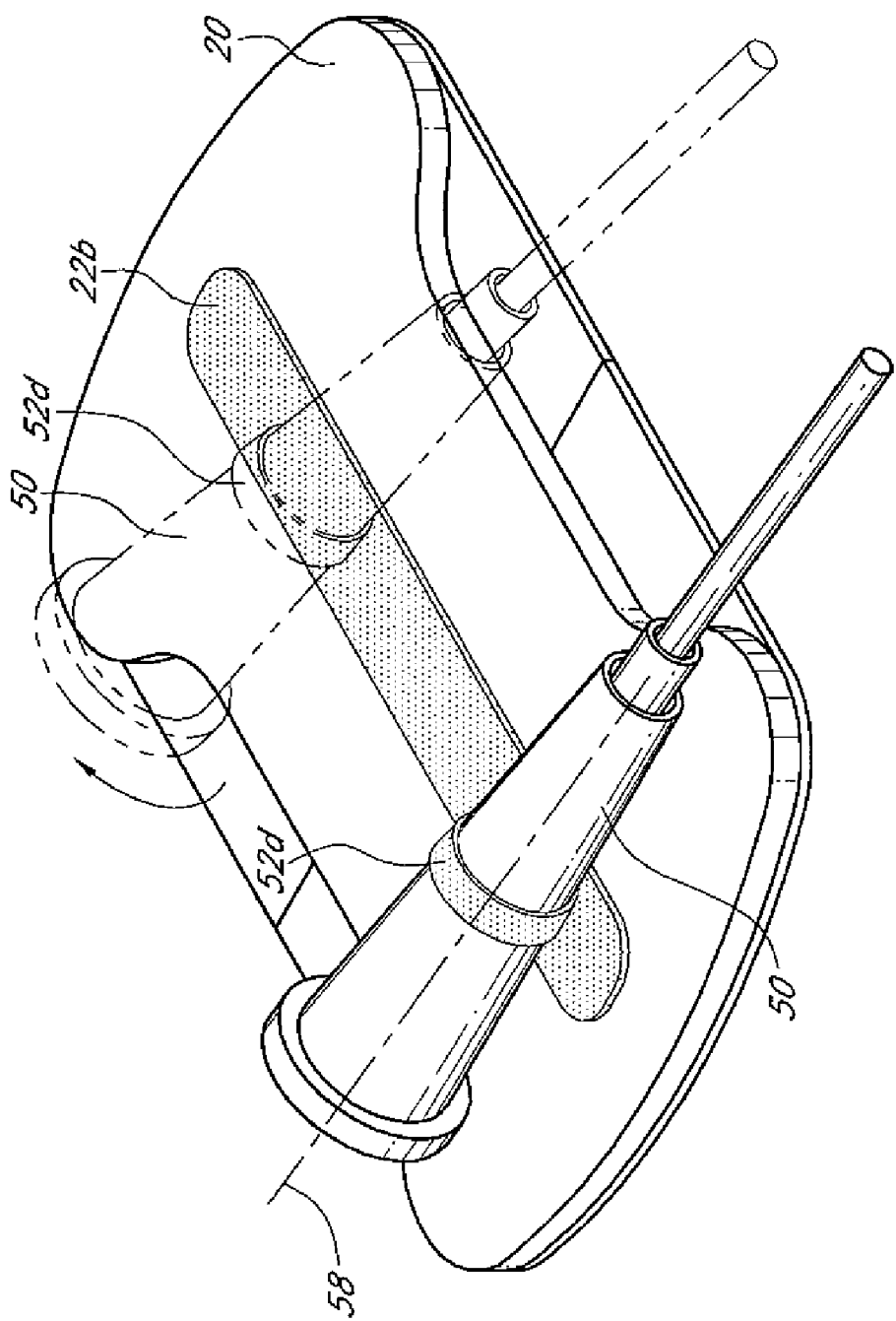
FIG. 10 is a perspective view of another preferred embodiment of the securement system of FIG. 1 and shows the catheter hub from FIG. 7 attached to the anchor pad from FIG. 3 in a plurality of positions.

FIG. 10 is a perspective view of another preferred embodiment of the securement system of FIG. 1 and shows the catheter hub 50 from FIG. 7 attached to the anchor pad 20 from FIG. 3 in a plurality of positions. Thus, not only may the attachment surface 52d be received at a plurality of areas on the attachment surface 22b, but the attachment surface 22b may engage with a plurality of receiving areas along the attachment surface 52d.

In this embodiment, it is possible to reposition the catheter 50 by rolling the catheter along the anchor pad 20. Thus, the catheter 50 may be repositioned on the anchor pad, rotated in a plane parallel to the anchor pad 20, and or rotated about the longitudinal axis 58 without disconnecting the catheter 50 from the anchor pad 20. By doing this, the likelihood that the catheter 50 will unintentionally become dislodged from the patient is decreased.

Those skilled in that art will appreciate that the catheter 50 may in some embodiments be turned in any direction in a plane substantially parallel to the anchor pad 20, shifted laterally, longitudinally, diagonally, or may be rotated about a longitudinal axis. Movement of the catheter 50 can also combine any or all of the motions. Thus, the catheter 50 can be positioned at any angle relative to the patient. In this way, the patient's comfort and the medical provider's ability to manipulate the catheter 50 are increased, as are the security of the attachment of the catheter 50 to the patient and the functionality of the catheter 50.

The securement system 10 can be provided as a kit that includes the catheter 50, the anchor pad 20, the attachment surface 22, and the attachment surface 52, all preassembled with the catheter 50 already attached to the anchor pad 20. In this configuration, the medical provided is only required to open the kit, administer the catheter 50, remove the release liner 32 if necessary, and press the securement system 10 against a patient's skin. To reposition the catheter 50, the catheter 50 is lifted to disengage the attachment surface 22 from the attachment surface 52. The catheter 50 may then be repositioned in a desired orientation.

The kit can include additional anchor pads 20 for placing the catheter 50 at different locations. The kit can also include additional attachment surfaces with adhesive backing to replace or supplement the existing attachment surfaces 22 and 52. The catheter 50 may also be provided with multiple pre-installed attachment surfaces, for example as illustrated in FIG. 6 or with one or more attachment surfaces mounted on the medical line 54.

Those skilled in the art will appreciate that the securement system 10 may reduce the need to precisely place the anchor pad 20 on the patient. Due to a plurality of receiving areas being possible, the catheter 50 may attach to the anchor pad 20 at a plurality of locations. Those skilled in the art will also appreciate that the need to precisely place the catheter 50 in relation to the anchor pad 20 may also be reduced. This greatly assists a medical provider, who is often attending to multiple tasks and does not always have time to carefully position the catheter, in properly securing and positioning the catheter 50 on the patient.

Figure 11:
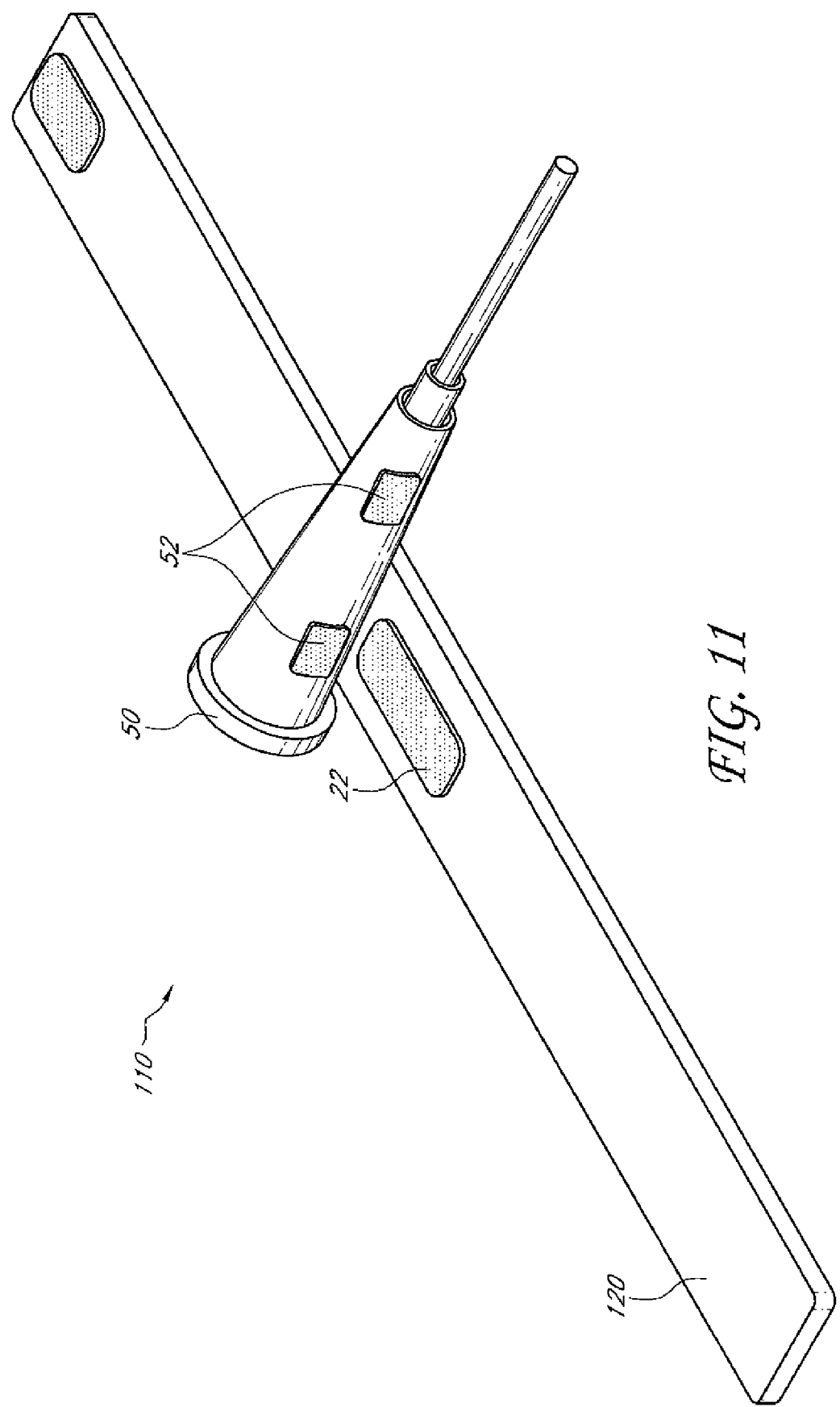
FIG. 11 is a perspective view of a securement system in accordance with another preferred embodiment of the present invention and shows a strap that has attachment surfaces for receiving the catheter hub.

With reference now to FIG. 11, another embodiment of a securement system 110 includes a strap 120 and the catheter 50. The strap 120 is configured to be secured to a patient, such as around a patient's limb. The catheter 50 is configured to attach to the strap 120 by engaging at least one of a plurality of the attachment surfaces 52 with the attachment surface 22.

FIGS. 12 and 13 illustrate an embodiment of the strap 120. The strap 120 is configured to wrap around a portion of the patient's body and attach to the patient. The length of the strap 120 is sufficient to be placed around an appendage of the patient. The length may be selected based on where the strap is to be attached to the patient's body, for example.

As can be seen in a top view of the strap in FIG. 12, an upper surface 122 of the strap 120 is configured to support the attachment surface 22. The attachment surface 22 is configured to engage with the attachment surface 52 on the catheter 50 and thereby secure the catheter 50. The attachment surface 22 may be attached to the strap 120 similar to any of the ways in which the attachment surface 22 is attached to the anchor pad 20, illustrated in FIG. 2. The attachment surface 22 and various configurations thereof have been described above.

In the illustrated embodiment, the upper surface 122 also supports a closure mechanism 124, which is configured to secure a first end 129a of the strap 120 to a second end 129b of the strap 120 by attaching to another closure mechanism 126. As can be seen in a bottom view of the strap 120 in FIG. 13, a lower surface 128 of the strap 120 supports the closure mechanism 126. The closure mechanisms 124 and 126 may be attached to the upper surface 122 and the lower surface 128, respectively, similar to the manner in which the attachment surface 22 is attached to the upper surface. The closure mechanisms 124 and 126 may also be integral to the upper surface 122 and/or the lower surface 128, respectively.

The lower surface 128 is configured for placement against the skin of the patient. Any number of medical materials may be used for this purpose, as is known by those skilled in the art. The upper surface 122 and the lower surface 128 may be integrally formed, or may be formed separately and attached together, such as by lamination. The strap 120 may comprise an elastic material or other material suitable for attachment to the patient.

The closure mechanisms 124 and 126 can be any devices or fasteners that are configured to attach the strap 120 about a portion of the patient's body. The closure mechanisms may be configured as complementary hook and loop fasteners or otherwise configured similar to the attachment surfaces 22 and 52, including the means by which the closure mechanisms 124 and 126 are attached to the strap. The closure mechanisms 124 and 126 may additionally comprise adhesive, a buckle, or a clip, for example.

In some embodiments, the upper surface 124 of the strap 120 is made of or covered entirely with a hook or loop material. In these embodiments, the catheter 50 may be attached to the strap 120 at any location along the upper surface 124. In addition, the closure mechanism 124 may be omitted if the closure mechanism 126 is configured with a complementary hook or loop material. Thus, the strap 120 could be attached around an appendage of a patient having virtually any circumference less than the length of the strap 120.

The shape and construction of the strap 120 may otherwise be varied. Any number of shapes or designs of the strap 120 are possible and within the scope of this description. For example, although the strap 120 is illustrated as being substantially uniform in width, the strap 120 may be shaped so as to be wider at its middle to provide a greater contact area with the patient. Although the strap 120 is illustrated as having substantially squared ends 129a and 129b, other embodiments include a strap with ends that are not squared or with a single squared end. One such embodiment is a strap with rounded ends, which may ease grasping the end 129b to remove the strap 120 from the patient. Although the strap 120 is illustrated as a single piece of material, the strap 120 may also comprise several pieces of material attached together.

Figure 14:
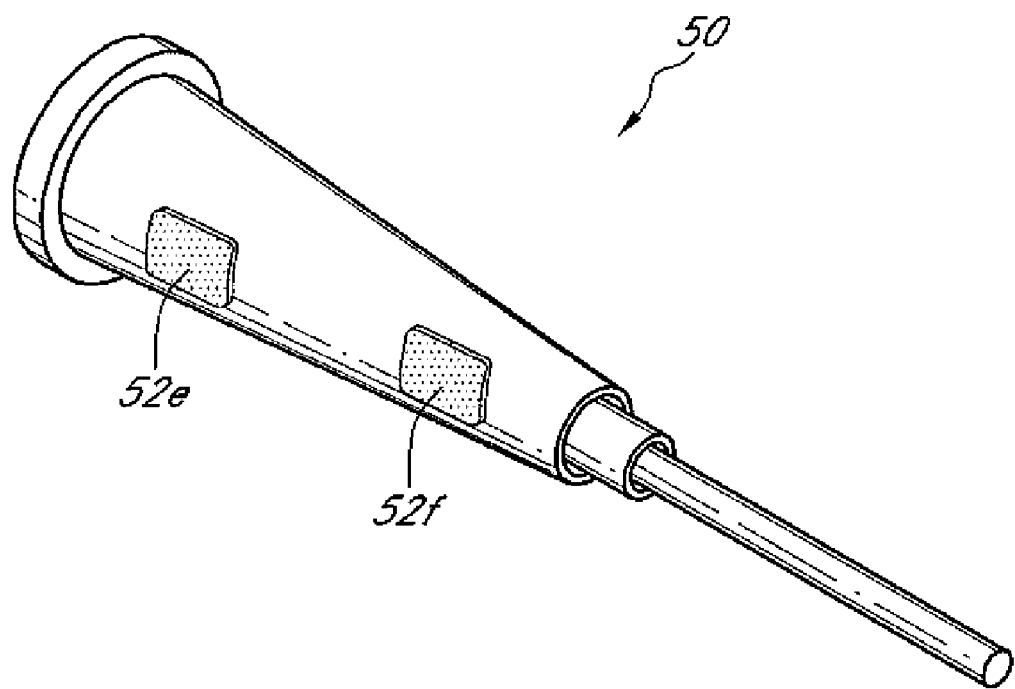
FIG. 14 is a perspective view of the catheter hub from FIG. 11 and shows a plurality of longitudinally spaced attachment surfaces disposed along the body of the hub.

FIG. 14 illustrates another embodiment of the catheter 50 and shows a plurality of attachment surfaces 52e and 52f that are longitudinally or axially spaced on the catheter 50. Disposing the attachment surfaces 52e and 52f in this way allows the catheter 50 to be attached to the strap 120, or the anchor pad 20, at a plurality of discrete longitudinal locations. By selecting one of the attachment surfaces 52e and 52f versus the other, the catheter 50 can be positioned closer or farther from an insertion site on the patient or proximal or distal end of the catheter 50 may be more closely secured to the strap 120 or anchor pad 20.

The attachment surfaces 52e and 52f may be spaced any distance apart on the catheter 50. The distance at which the attachment surfaces 52e and 52f are spaced may be selected according to any number of factors, such as intended use of the catheter 50 or according to what type of medical article the attachment surfaces 52e and 52f are being disposed on.

Two discrete attachment surfaces 52e and 52f are illustrated in FIG. 14. There may, however, be any number of attachment surfaces disposed axially along the catheter 50. For example, three or five attachment surfaces may be disposed on the catheter 50. In addition, the attachment surfaces 52e and 52f are illustrated as being shaped similar to the attachment surface 52a, illustrated in FIG. 5. The attachment surfaces 52e and 52f may be configured similar to the attachment surface 52a or the attachment surfaces 52e and 52f may be any other shape.

Figure 15:
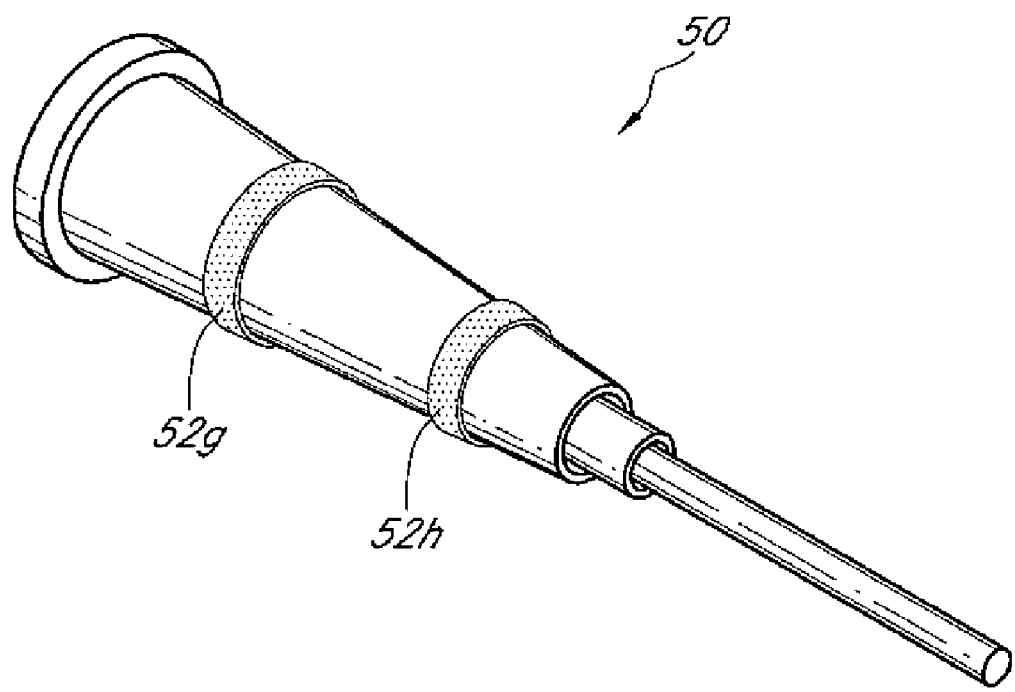
FIG. 15 is a perspective view of another embodiment of the catheter hub from FIG. 5 and shows a plurality of longitudinally spaced attachment surfaces configured as annular rings around the body of the hub.

FIG. 15 illustrates another embodiment of the catheter 50 including a plurality of attachment surfaces 52g and 52h that are longitudinally spaced. In this embodiment, the attachment surfaces 52g and 52h are illustrated as being similar to the attachment surface 52d, illustrated in FIG. 7, although the attachment surfaces 52g and 52h may be configured differently.

Longitudinally spaced attachment surfaces, such as the attachment surfaces 52e and 52f or the attachment surfaces 52g and 52h, may be similarly shaped or may have differing shapes. For example, the catheter 50 may include one attachment surface that is shaped similar to the attachment surface 52a, and may also include one attachment member that is shaped similar to the attachment surface 52d.

The catheter 50 may include circumferentially spaced attachment surfaces in addition to or in place of axially spaced attachment members. Spaced attachment members do not need to be disposed linearly or circularly, but can be disposed in any pattern or configuration. The attachment surfaces 52e-52h are illustrative embodiments of the attachment surface 52 only and are not limiting in any way.

A medical provider can use the securement system 110 in ways similar to ways in which the securement system 10 is used, such as illustrated in FIG. 8. To attach the strap 120 to the patient, however, the strap 120 is wrapped around a portion of the patient's body, such as around an appendage. Then, the closure mechanisms 124 and 126 can be engaged to secure the strap 120 about the portion of the patient's body. The closure mechanisms 124 and 126 can be disengaged in some embodiments and the position of the strap 120 adjusted relative to the patient's body. In other embodiments, the strap 120 may have to be severed to be removed from the patient.

Figure 16:
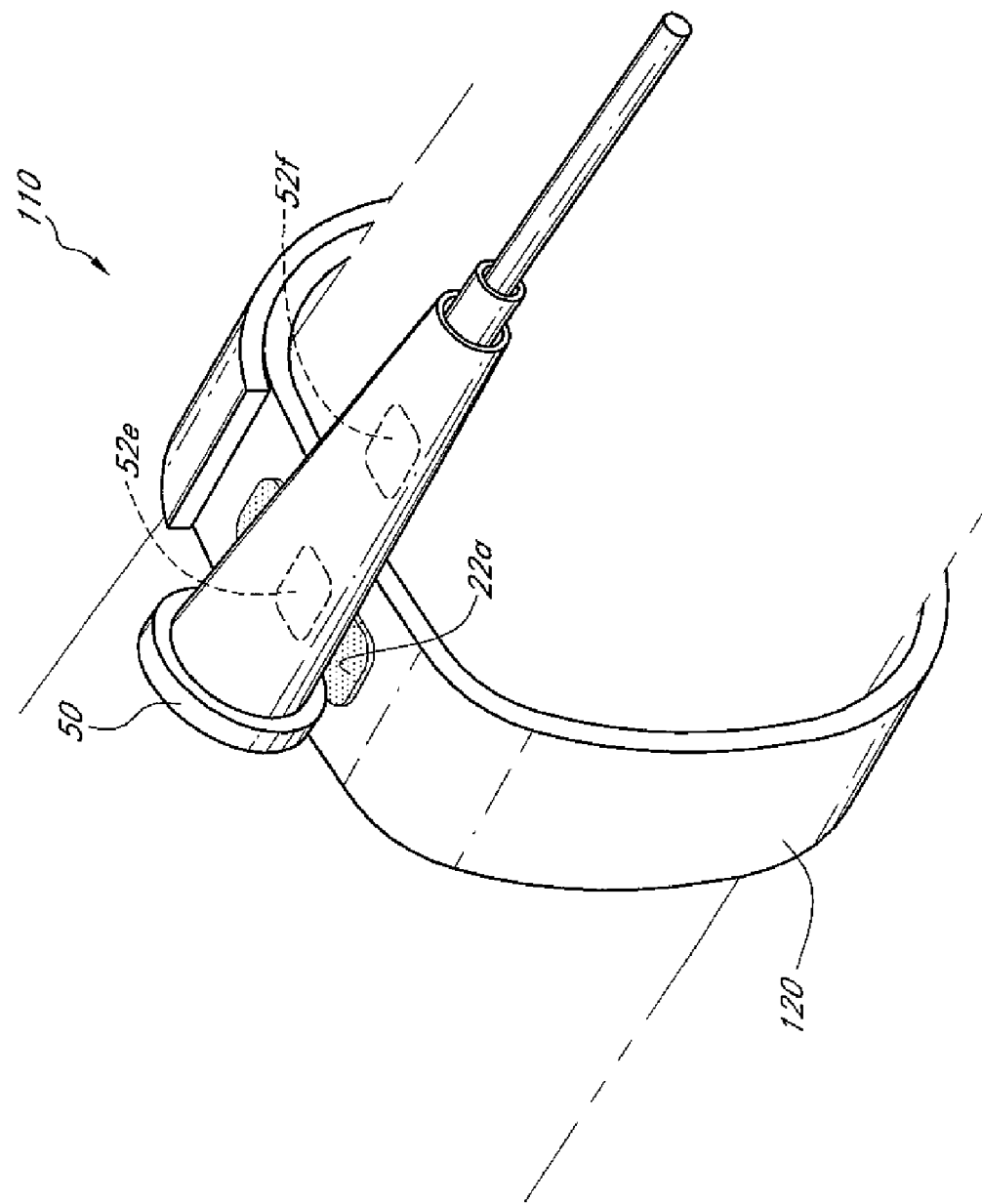
FIG. 16 is a perspective view of the securement system from FIG. 11 attached to a patient and shows the catheter hub from FIG. 14 attached to the strap in a first position.

As can be seen in FIG. 16, the catheter 50 may be secured on the strap 120 at a first location by engaging one of the attachment surfaces 52 with the attachment surface 22. In the illustrated embodiment, the attachment surface 52e may be secured at a plurality of receiving areas on the attachment surface 22a.

Figure 17:
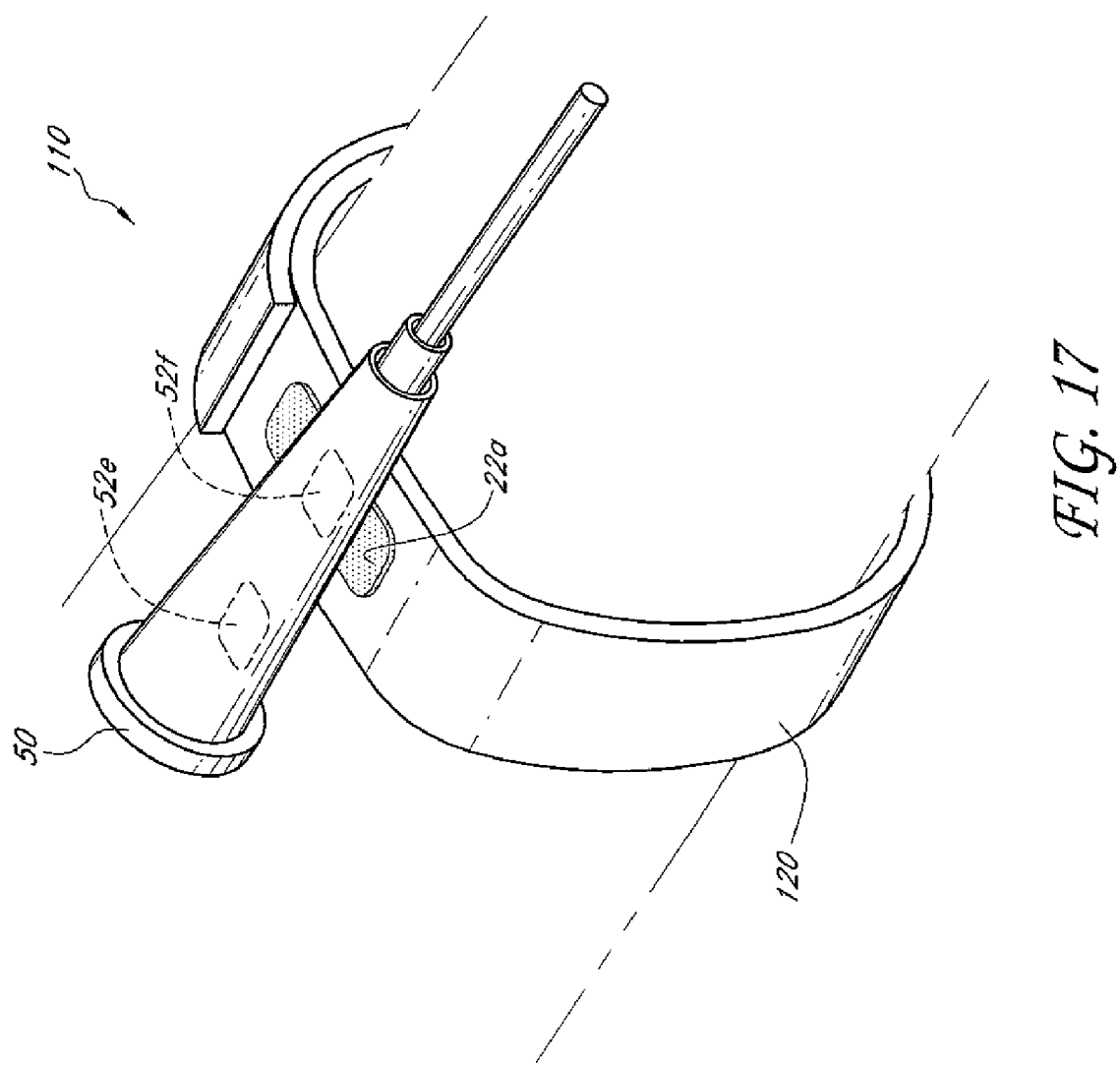
FIG. 17 is a perspective view of the securement system from FIG. 16 after the catheter hub has been moved from the first securement position to a second securement position.

After disengaging the catheter 50 from the strap 120, the catheter 50 may be secured to the strap 120 at a second location, as can be seen in FIG. 17. In the illustrated embodiment, the attachment surface 52f may be secured at a plurality of receiving areas on the attachment surface 22a. When the catheter 50 is attached to the strap 120 in this way, the distal end of the catheter 50 will be secured closer to the strap 120. In both the first and second positions, the catheter 50 may be attached in a plurality of rotations within the plane of the attachment member 22a.

Similar to the securement system 10, the catheter 50 may be attached to the strap 120 before or after the strap 120 is attached to the patient. In addition, the catheter 50 may be disengaged and reengaged at a plurality of receiving areas or at a plurality of rotations, as in the securement system 10. Also, the securement system 110 may similarly come preassembled or packaged in a kit and may include additional components.

Those of skill in the art will understand that all descriptions above relating to attaching the catheter 50 to the strap 120 can similarly apply to the securement system 10 in which the catheter 50 attaches to the anchor pad 20. Similarly, the description of the catheter 50 attaching to the anchor pad 50 applies to the catheter 50 being able to attach to the strap 120. To add to this, either the anchor pad 20 or the strap 120 may be supplemented or replaced by another structure that supports the attachment surface 22 and is configured to attach to the patient, such as a rigid base.

Figure 18:
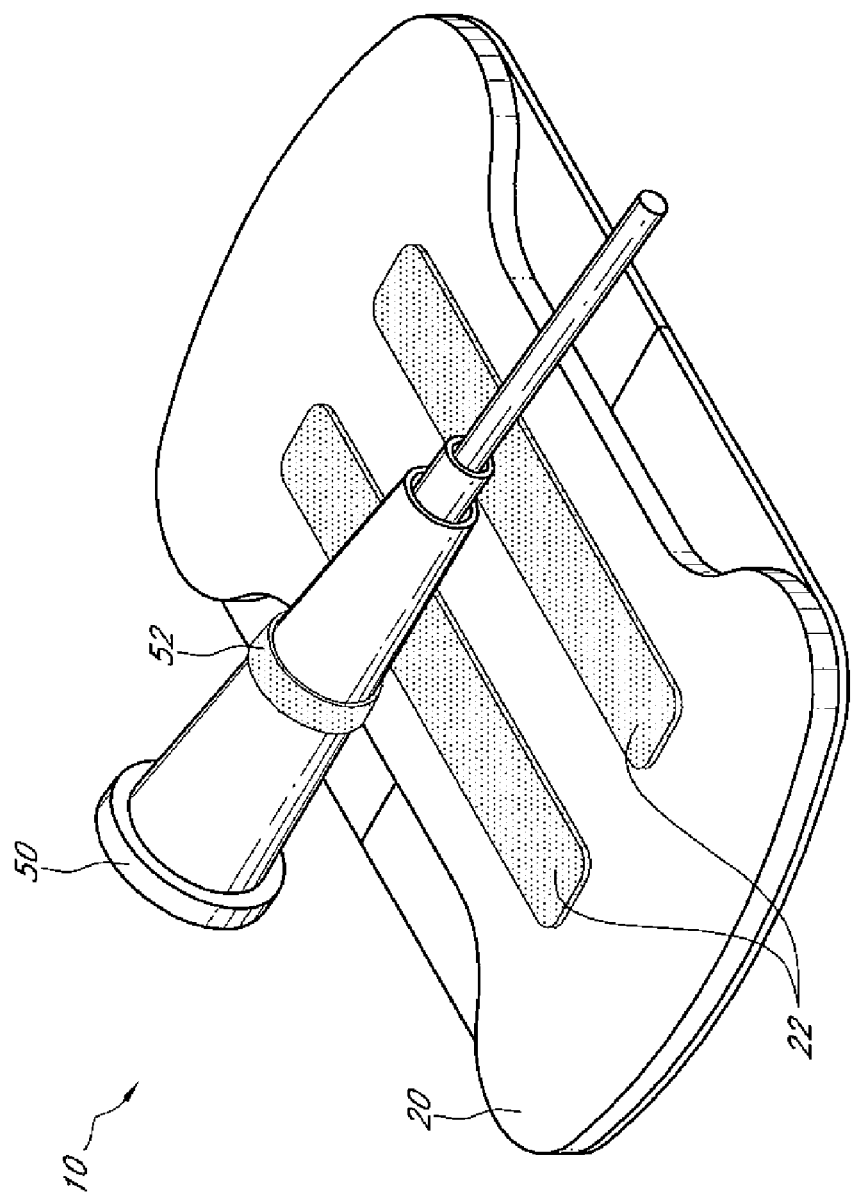
FIG. 18 is a perspective view of a securement system in accordance with another preferred embodiment of the present invention and shows an anchor pad that has two laterally extending attachment surfaces for receiving the attachment surface of the catheter hub.

With reference now to FIG. 18, another embodiment of the securement system 10 includes the anchor pad 20, which is configured with a plurality of the attachment surfaces 22, and the catheter 50. The catheter 50 is configured to attach to the anchor pad 20 by engaging at least one of the plurality of the attachment surfaces 22 with the attachment surface 52.

Figure 19:
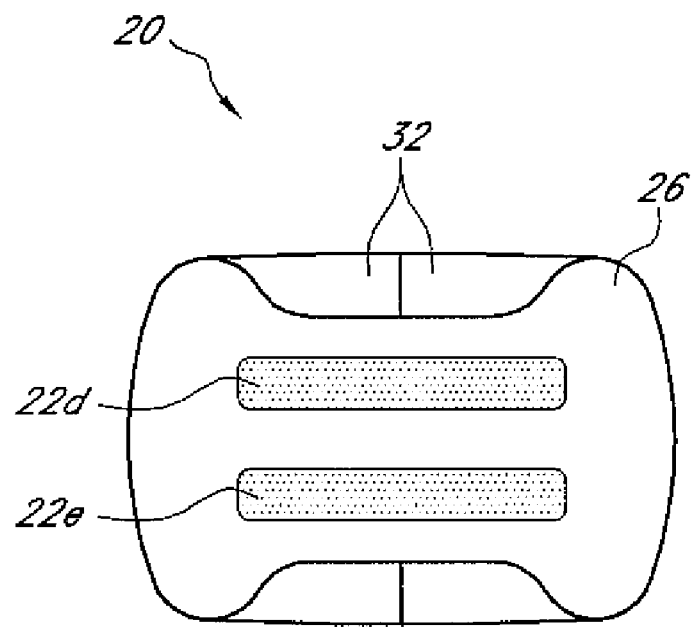
FIG. 19 is a top view of the anchor pad from FIG. 18 and shows the two laterally extending attachment surfaces.

FIG. 19 illustrates another embodiment of the anchor pad 20 and shows a plurality of attachment surfaces 22d and 22e. The attachment surfaces 22d and 22e are disposed at similar lateral locations on the anchor pad 20, but are disposed at differing longitudinal locations. Disposing the attachment surfaces 22d and 22e in this way allows the catheter 50 to be attached to the anchor pad 20 at a plurality of discrete longitudinal locations, while allowing ample lateral placement. By selecting one of the attachment surfaces 22d and 22e versus the other, the catheter 50 can be positioned closer or farther from an insertion site on the patient.

The attachment surfaces 22d and 22e may be spaced any distance apart on the anchor pad 20. The distance at which the attachment surfaces 22d and 22e are spaced may be selected according to any number of factors, such as intended use of the securement system 10 or according to what type of medical article may be attached to the anchor pad 20.

The attachment surfaces 22d and 22e are illustrated as being shaped similar to the attachment surface 22b, illustrated in FIG. 3. The attachment surfaces 22d and 22e may be configured similar to the attachment surface 22b or the attachment surfaces 22d and 22e may be any other shape.

FIG. 15 illustrates another embodiment of the anchor pad 20 including a plurality of attachment surfaces 22f, 22h, 22g, and 22i and shows the attachment surfaces 22f-22i spaced at a various lateral and longitudinal locations. In this embodiment, the attachment surfaces 22f-22i are illustrated as being similar to the attachment surface 52a, illustrated as being disposed on the catheter 50 in FIG. 5.

Configuring the attachment surfaces 22f-22i similar to the attachment surface 52a reduces the number or areas at which the catheter 50 may be received. When the attachment surfaces 22f-22i are small, as illustrated in the present embodiment, the catheter 50 can only be connected to the anchor pad 20 at a discrete number of lateral and longitudinal locations. Thus, the placement of the catheter 50 will be limited to a predetermined plurality of locations. The catheter, 50, however, will still be able to be attached at any rotational direction within the plane of the anchor pad 20 at any of the attachment surfaces 22f-22i.

A plurality of the attachment surfaces 22, such as the attachment surfaces 22d-22i, may be similarly shaped or may have differing shapes. For example, the anchor pad 20 may include one attachment surface that is shaped similar to the attachment surface 22a, and may also include one attachment member that is shaped similar to the attachment surface 22b. The plurality of the attachment surfaces 22 may take any shape.

The plurality of the attachment surfaces 22 may be arranged on the anchor pad 20 in any pattern or configuration or the plurality of the attachment surfaces 22 may be arranged on the anchor pad 20 at random. The plurality of the attachment surfaces 22 may be spaced at any distance and may be attached to any lateral or longitudinal locations on the anchor pad 20.

Figure 20:
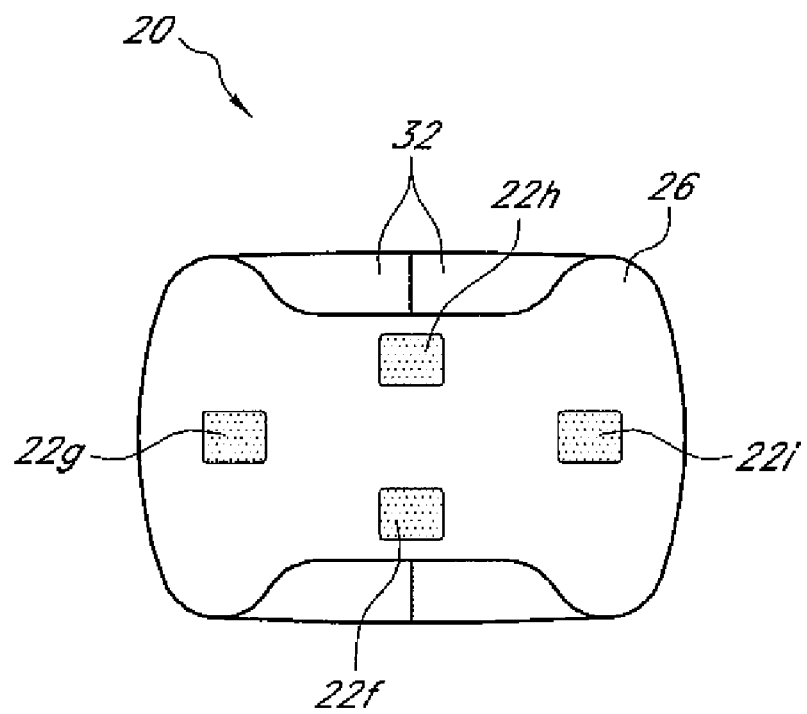
FIG. 20 is a top view of another embodiment of the anchor pad from FIG. 19 and shows four attachment surfaces spaced in a diamond shape on the anchor pad.

Any number the attachment surfaces may be mounted on the anchor pad 20. FIGS. 19 and 20 illustrate two and four of the attachment surfaces 22, respectively, but any other could be attached. For example, seven, eight, or nine of the attachment surfaces 22 may be disposed on the anchor pad 20.

Figure 21:
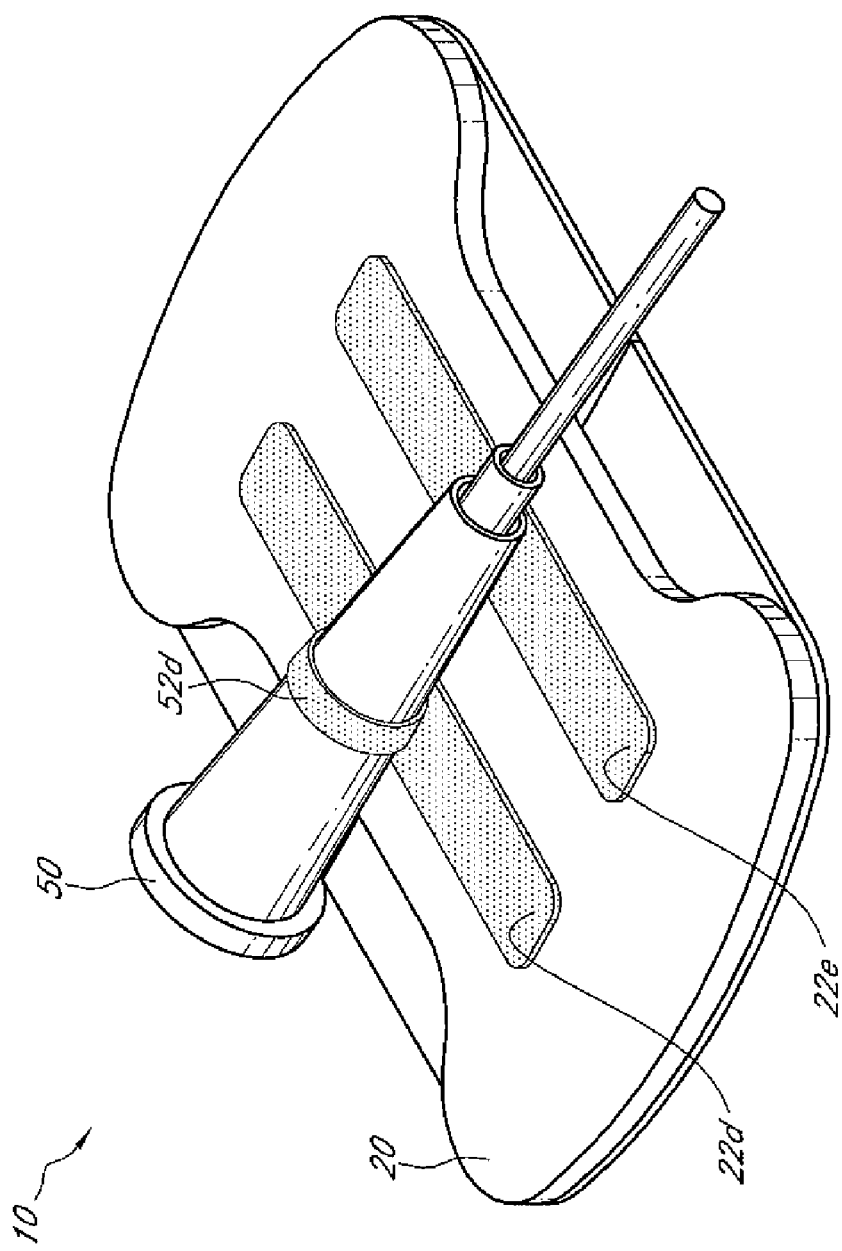
FIG. 21 is a perspective view of the securement system from FIG. 18 and shows the attachment surface of the catheter hub attached to one of the two attachment surfaces of the anchor pad in a first position.

As can be seen in FIG. 21, the catheter 50 may be secured to the anchor pad 20 at a first location by engaging the attachment surface 52 with one of the attachment surfaces 22. In the illustrated embodiment, the attachment surface 52d may be secured at a plurality of receiving areas on the attachment surface 22d.

Figure 22:
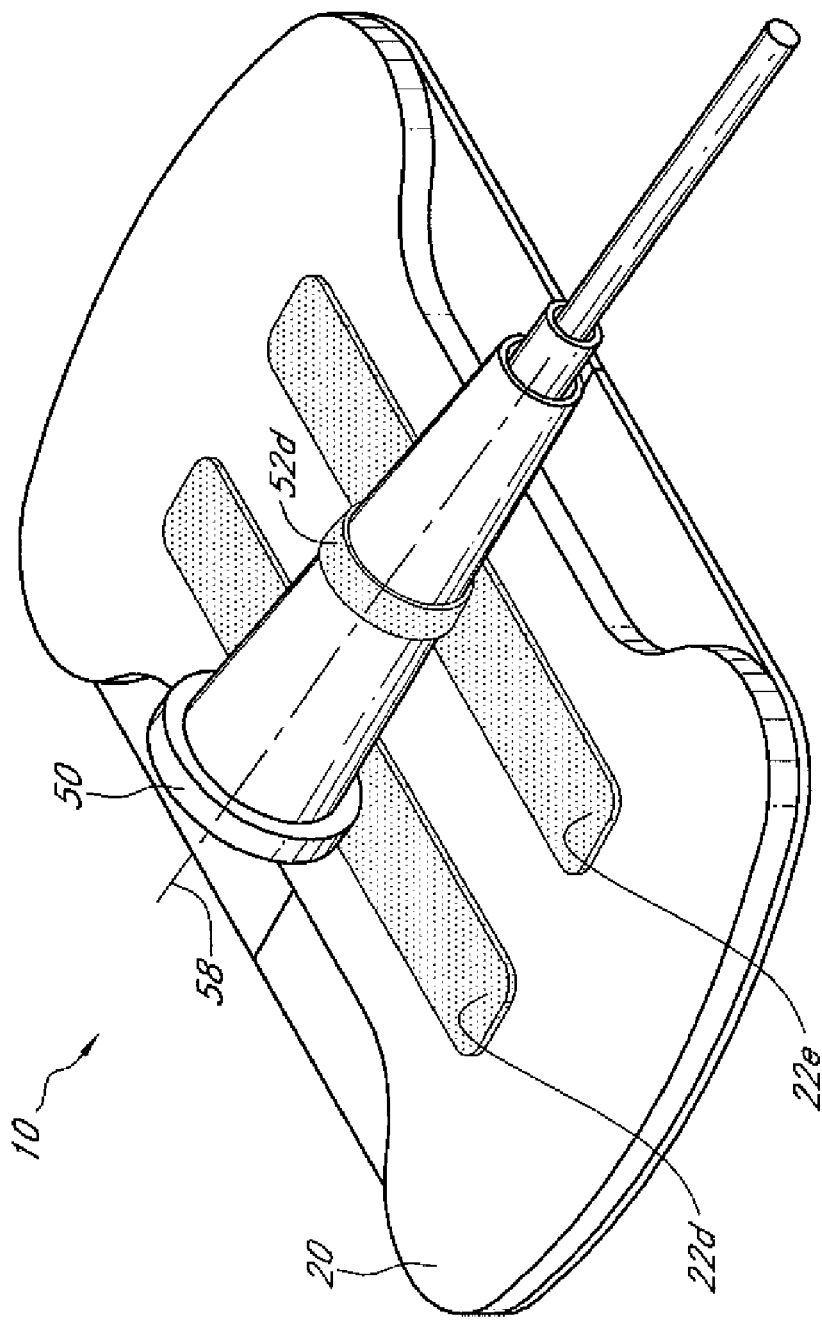
FIG. 22 is a perspective view of the securement system from FIG. 21 after the catheter hub has been moved from the first securement position to a second securement position.

After disengaging the catheter 50 from the anchor pad 20, the catheter 50 may be secured to the anchor pad 20 at a second location, as can be seen in FIG. 22. In the illustrated embodiment, the attachment surface 52d may be secured at a plurality of receiving areas on the attachment surface 22e. When the catheter 50 is attached to the anchor pad 20 in this way, the catheter 50 will be secured closer to a distal side of the anchor pad 20. In both the first and second positions, the catheter 50 may be attached in a plurality of rotations within the plane of the anchor pad 20 and may be rotated about the longitudinal axis 58 by any amount.

Figure 23:
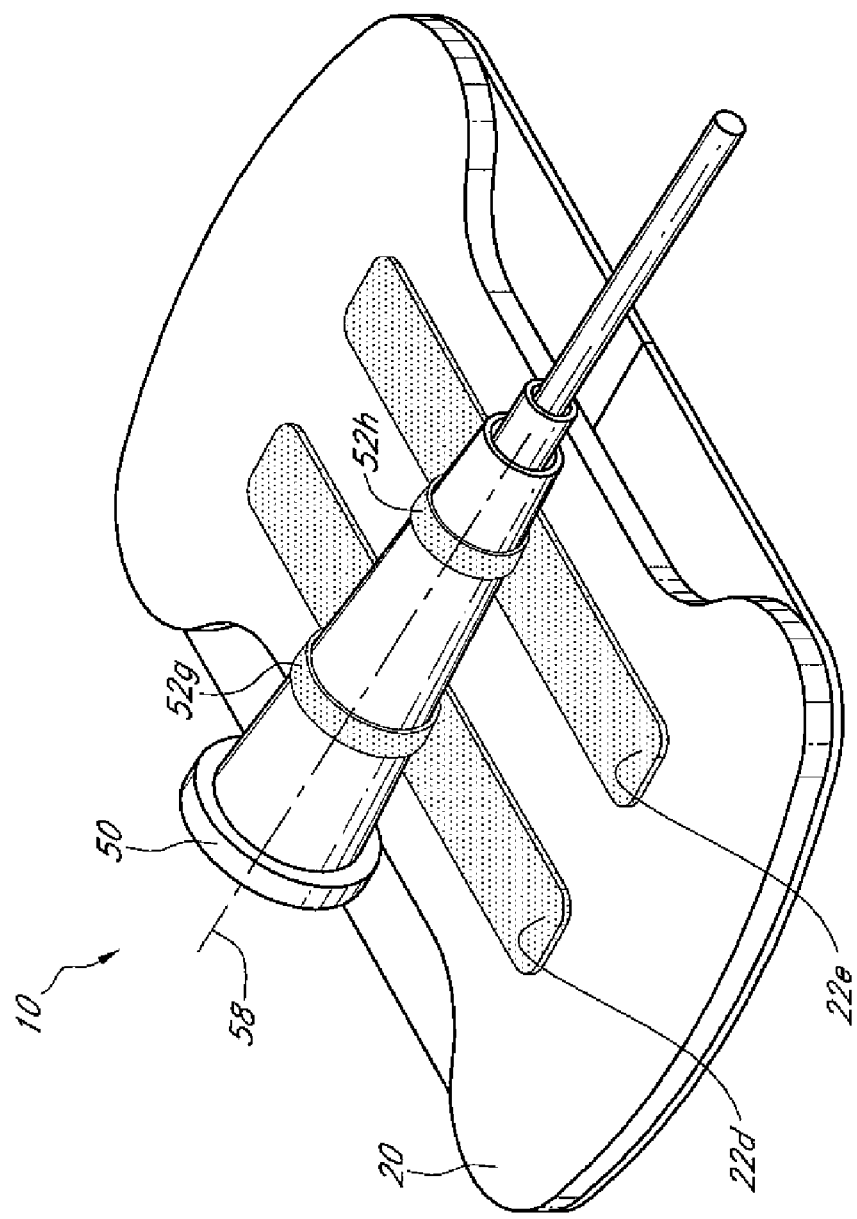
FIG. 23 is a perspective view of another embodiment of the securement system from FIG. 18 and shows the catheter hub from FIG. 15 attached to the anchor pad from FIG. 19 at a plurality of securement locations.

Of course, the securement system may simultaneously include a plurality of the attachment surfaces 22 mounted on the anchor pad 20 and a plurality of the attachment surfaces 52 mounted on the catheter 50. This configuration is shown in FIG. 23. The anchor pad 20 is illustrated as having the attachment surfaces 22d and 22e, as illustrated in FIG. 18, and the catheter 50 is illustrated as having the attachment surfaces 52g and 52h, as illustrated in FIG. 15.

Either or both of the attachment surfaces 52g and 52h may engage either of the attachment surfaces 22d and 22e. Thus, the catheter 50 may be connected to the anchor pad 20 by two, three, or four engaged attachment surfaces. In the illustrated embodiment, all four of the attachment surfaces 22d, 22e, 52g, and 52h are engaged.

There may be any number of the attachment surfaces 22 and any number of the attachment surfaces 52. Although an equal number of the attachment surfaces 22 and the attachment surfaces 52 are illustrated, there may a great number of either. Any number of the attachment surfaces 22 may engage any other number of the attachment surfaces 52.

Figure 24:
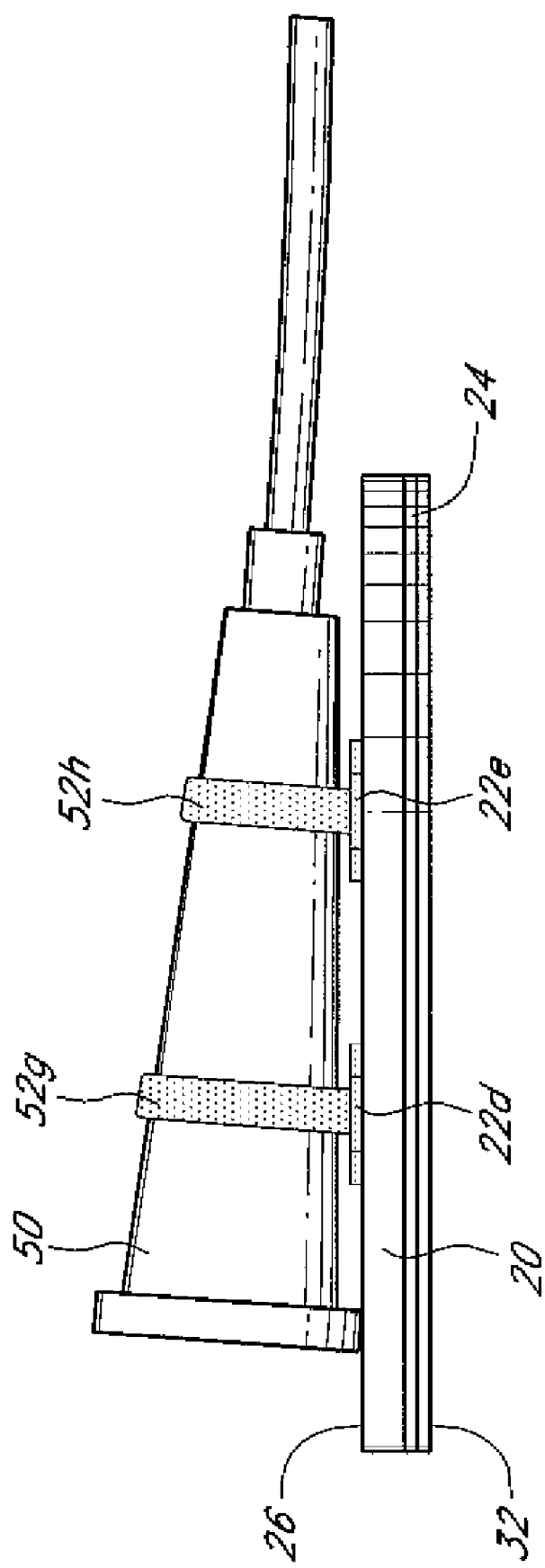
FIG. 24 is a side view of the securement system from FIG. 23 and shows the attachment surfaces of the catheter hub attached to the attachment surfaces of the anchor pad.

The attachment surfaces 22 and the attachment surfaces 52 may be respectively arranged in any pattern with any number of shapes. Although the attachment surfaces 22 and the attachment surfaces 52 are illustrated as being disposed so that they may be substantially aligned, as shown in a side view of the system 10 in FIG. 24, the attachment surfaces 22 and the attachment surfaces 52 may be disposed in any other way.

When a plurality of the attachment surfaces 22 and a plurality of the attachment surfaces 52 are provided, the catheter 50 may still be affixed to the anchor pad 20 at any position rotated within the plane of the anchor pad. In some embodiments, the catheter 50 can still be affixed to the anchor pad in any configuration rotated about the axis 58 and/or the catheter 50 can still be rolled along the anchor pad 20 without disengaging from the anchor pad 20. When a plurality of the attachment surfaces 52 is engaged, however, the catheter 50 may be further inhibited from unintentional movement. For example, when two attachment surfaces 52 spaced longitudinally along the catheter 50 are engaged, the dual points of attachment to the anchor pad 20 will inhibit any unintentional rotation and the increased number of attachments will further inhibit motion in all directions.

Figure 25:
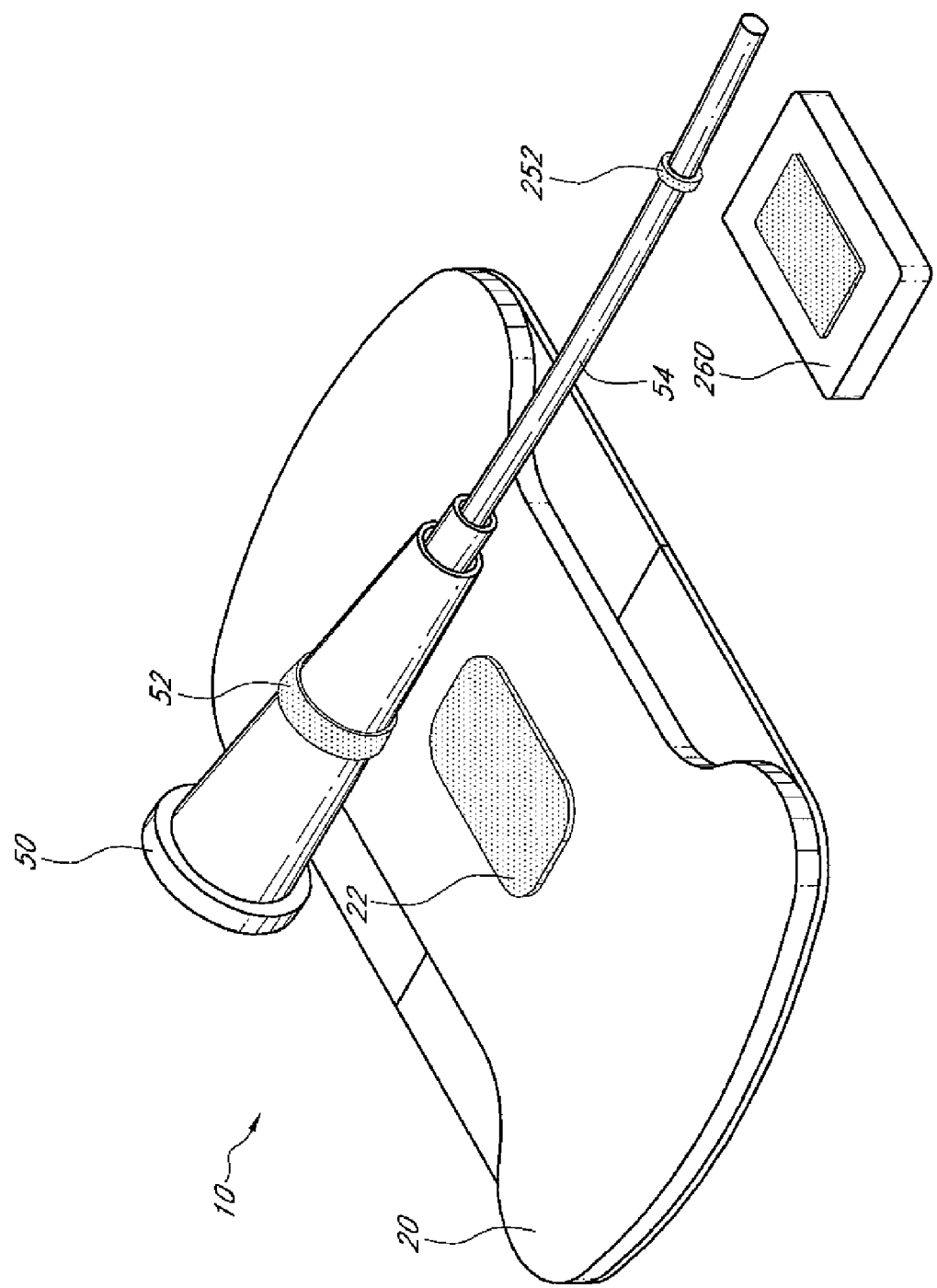
FIG. 25 is a perspective view of a securement system in accordance with another embodiment of the present invention and shows a catheter hub, anchor pad, and auxiliary anchor pad prior to the securement of the catheter hub onto the pads.

With reference now to FIG. 25, another embodiment of the securement system 10 includes the anchor pad 20 and the catheter 50, and further includes an auxiliary anchor pad 260. The auxiliary anchor pad is configured to engage a portion of the catheter or another medical article located farther along medical line 54. The portion of the catheter or the other medical article located farther along the line 54 may include an auxiliary attachment surface 252 to facilitate connection to the auxiliary anchor pad 260.

Figure 26:
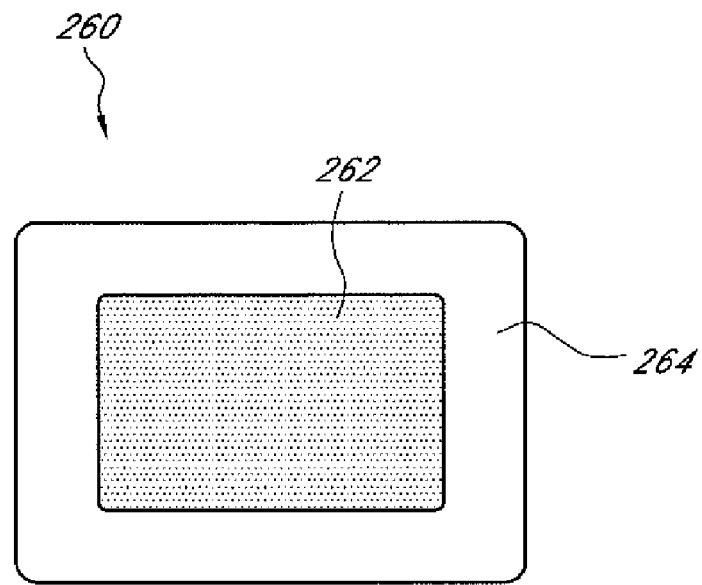
FIG. 26 is a top view of the auxiliary anchor pad from FIG. 25 and shows an attachment surface.

FIG. 26 illustrates an embodiment of the auxiliary anchor pad 260. The auxiliary anchor pad has an attachment surface 262 mounted on an upper layer 264 of the auxiliary anchor pad 260.

The auxiliary anchor pad 260 may be configured as any size or shape. In the illustrated embodiment, the auxiliary anchor pad 260 is substantially rectangular and is sized smaller than the anchor pad 20. Shaping the anchor pad in this way limits the size of the auxiliary anchor pad to the illustrated shape of the attachment surface 262, whereby little of the upper layer 264 is exposed beyond the attachment surface 262. Of course, the upper layer 264 may be sized and shaped similar to the attachment surface 262.

The smaller size may allow the auxiliary anchor pad 260 to be placed in areas in which the anchor pad 20 may not. In addition, the anchor pad may not need to secure as large or as heavy a medical article, such as when the auxiliary anchor pad is used only to secure the medical line 54. The auxiliary anchor pad 260 may otherwise be configured similar to the anchor pad 20.

The attachment surface 262 is configured to engage the auxiliary attachment surface 252, for example using complementary hook and loop fasteners. The auxiliary attachment surface 252 may be disposed on any portion of the catheter 50 or another medical device and may have any size or shape. In FIG. 25, the auxiliary attachment surface 252 encircles the medical line 54 and has an annular shape. The auxiliary attachment surface 252 has hook or loop fasteners attached to an other portion of the annular shape such that any outer portion may engage the attachment surface 262.

The attachment surface 262 and the auxiliary attachment surface 252 may otherwise be configured similar to the attachments surfaces 22 and/or 52, including the means by which the attachment surface 262 is attached to the auxiliary anchor pad 260 and the means by which the auxiliary attachment surface 252 is attached to the catheter 50 or other medical article. The attachment surface 262 may be integral to the upper layer 264 of the auxiliary anchor pad 260.

Figure 27:
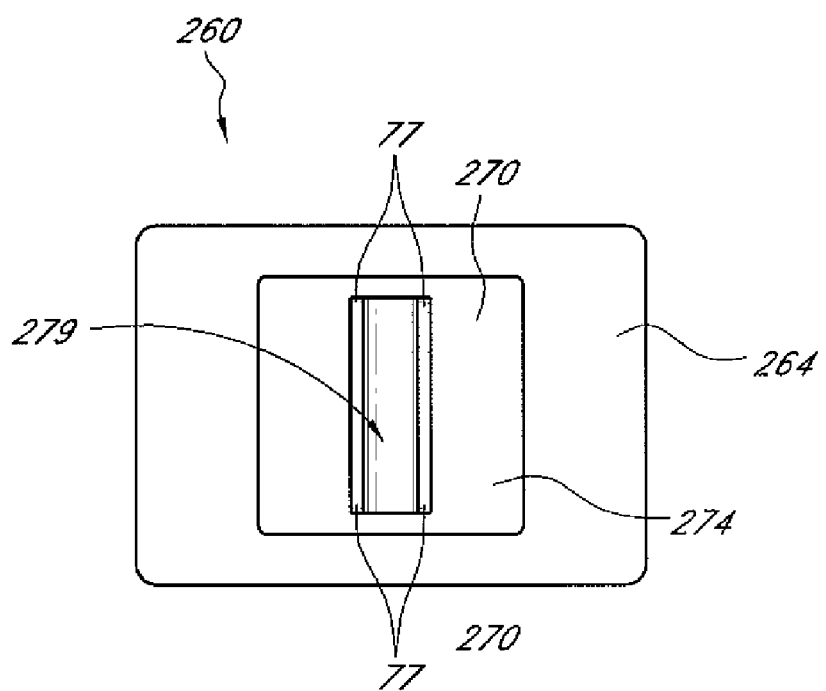
FIG. 27 is a top view of another embodiment of the auxiliary anchor pad from FIG. 26 and shows a clip on an upper surface of the anchor pad.
Figure 28:
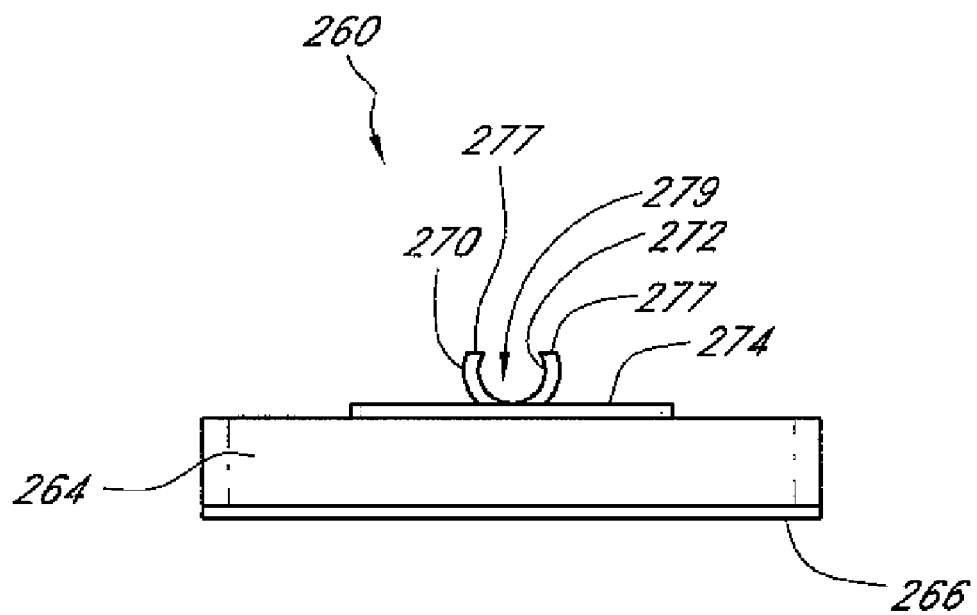
FIG. 28 is a front view of the auxiliary anchor pad from FIG. 27.
Figure 29:
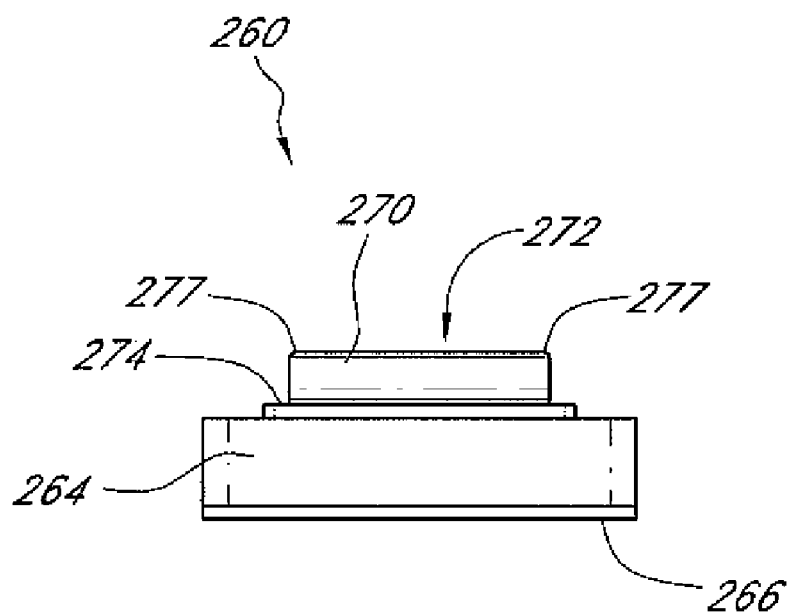
FIG. 29 is a side view of the auxiliary anchor pad from FIG. 27.

FIGS. 27 through 29 illustrate another embodiment of the auxiliary anchor pad 260 and show a tube clip 270 mounted on the upper layer 264 of the anchor pad 260. As can be seen in a top view of the auxiliary anchor pad 260 in FIG. 27, the tube clip 270 has a plate-like base 274 adhered to or embedded in the upper layer 264 of the auxiliary anchor pad 260. The clip 270 secures a fluid supply tube, such as the medical line 54, as is known in the art.

As can be seen in FIGS. 28 and 29, the anchor pad 260 includes a lower adhesive layer 266 configured to attach to the patient. The lower adhesive layer 266 may be configured similar to the lower adhesive layer 26 of the anchor pad 20. A release liner (not shown) similar to the release liner 32 may be attached to the lower adhesive layer 266.

As can be seen in a front view of the auxiliary anchor pad 260 in FIG. 28, the clip 270 defines a channel 272 having a generally circular cross-sectional configuration truncated to form an opening 279. The diameter of the channel 272 is desirably slightly less than that of the medical line 54 so as to ensure a secure interconnection. The channel 272 receives a portion of the medical line 54 through the opening 279 upon application of gentle pressure or by pulling the line 54 across and through the opening 279 of the tube clip 270, as explained below. The clip 270 thereafter surrounds a portion of the line 54. The sides of the channel 272 may be angled in relation to themselves or in relation to each other to accommodate a different medical line or other medical article.

As seen in a side view of the auxiliary anchor pad 260 in FIG. 29, the upper edge of the channel includes tapered ends 277 at the proximal and distal ends of the clip 270. Each tapered end 277 forms a smooth transition between the side edge of the channel 272 and the upper edge, and tapers in lateral width from the side edge toward the center of the tube clip 270. The tapered ends 277 help guide the medical line 54 into the channel 272 when a medical provider pulls the tube across the clip 270. Thus, the medical provider does not have to pinch the line 54 to insert it into the clip 270. Also, the medical provider's gloves do not get stuck in the clip 270 when inserting the line 54, as is typically the case where the medical provider is required to pinch the line 54 to insert it into the clip 270.

Figure 30:
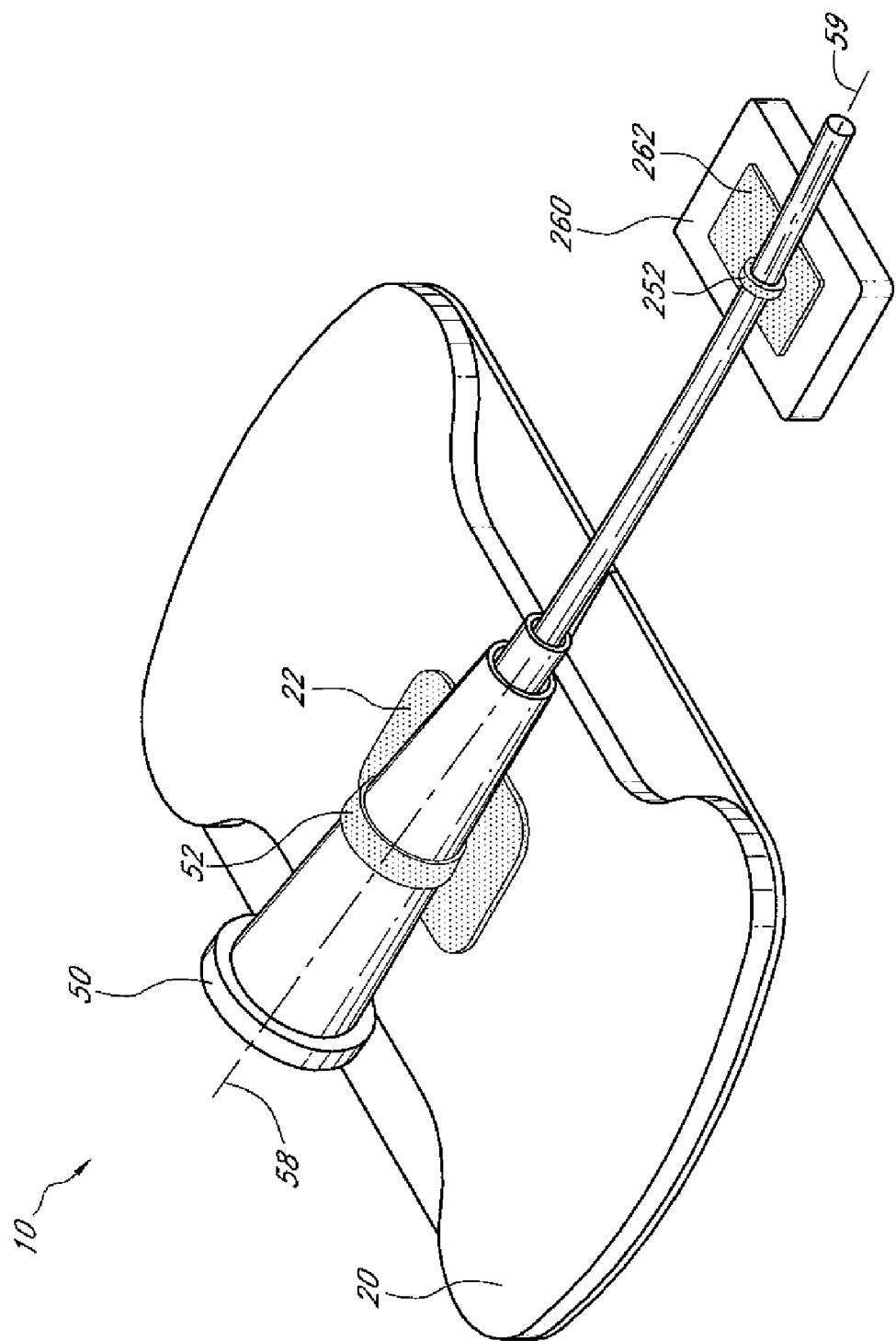
FIG. 30 is a perspective view of the securement system from FIG. 25 with the catheter hub attached to both the anchor pad and the auxiliary anchor pad.

As can be seen in FIG. 30, the catheter 50 can connect to the anchor pad 20 as described above. In addition, the auxiliary attachment surface 252 can engage the attachment surface 262 of the auxiliary anchor pad 260 when the auxiliary attachment surface 252 is pressed against the attachment surface 262. Such engagement may be performed similarly to engaging the attachment surface 52 with the attachment surface 22, and disengagement of the auxiliary attachment surface 252 from the attachment surface 262 can be performed similarly to disengaging the attachment surface 52 from the attachment surface 22.

In the illustrated embodiment, the auxiliary attachment surface 252 may be connected to the attachment surface 262 at a plurality of locations spaced laterally and longitudinally across the auxiliary anchor pad 260. Thus, the orientation of the medical line 54 alone or in combination with the rest of the catheter 50 may be adjusted.

In the illustrated embodiment, the medical line 54 may also be rotated about a longitudinal axis 59 and attached to the attachment surface 262 at any such rotated orientation. Thus, the line 54 alone or in combination with the rest of the catheter 50 can be rotated to for attachment or disengaged and rotated for reattachment. The auxiliary attachment surface 252 can be caused to engage the attachment surface 262 before, after, or substantially simultaneously with a time when the attachment surface 52 is caused to engage the attachment surface 22.

Figure 31:
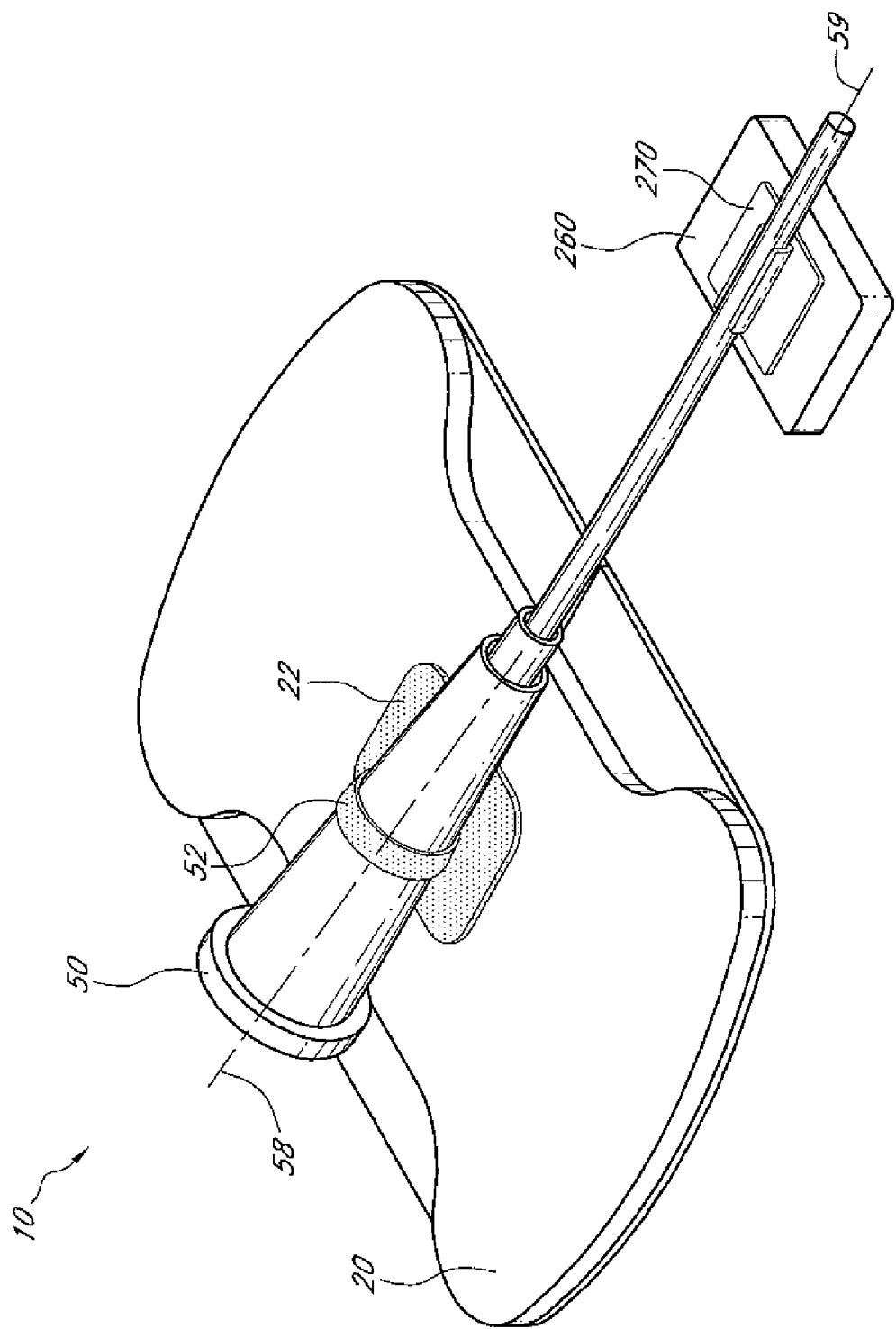
FIG. 31 is a perspective view of another embodiment of the securement system from FIG. 25 with the catheter hub attached to the anchor pad and the auxiliary anchor pad from FIG. 27.

As can be seen in FIG. 31, the medical line 54 can be retained by the clip 270 of the auxiliary anchor pad 260 concurrently with the catheter 50 being attached to the anchor pad 20. The method of securing the line 54 in the clip 270 has already been described above. The line 54 can be caused to engage the clip 270 before, after, or substantially simultaneously with a time when the attachment surface 52 is caused to engage the attachment surface 22.

To disengage the tube 54 from the clip 270, a medical provider need only pull the line 54 towards the opening 279 with sufficient force, possibly by holding either end of the line 54 extending from the clip 270. Those of skill in the art will appreciate that prior to the line 54 being disengaged from the clip 270, the clip 270 will align the line 54 in a direction determined by the placement of the auxiliary anchor pad 260 and the clip 270.

The channel 272 is preferably shaped to inhibit rotation of the medical line 54 within the tube clip 270. In this way, the line 54 can be properly secured. In some embodiments, the channel 272 is sized and or shaped to allow the line 54 to spin within the clip 270. Thus, lateral motion of the line 54 is inhibited, but the line 54 may rotate about the longitudinal axis 59 alone or in combination with the rest of the catheter 50. Of course, the body of the catheter 56 and the line 54 may be configured to allow rotation about a longitudinal axis either independent of each other or solely in combination.

In situations where the channel 272 of the clip 270 is sized and shaped to allow the medical line 54 to spin within the clip 270, but such spin is not desired, a tube with the auxiliary attachment surface 252 may be inserted (not shown) in the clip 270. The girth added to the line 54 by the auxiliary attachment surface 252 may sized or shaped substantially similar to the size or shape of the channel 272, and thereby inhibit the line 54 from spinning within the clip 270.

Both the attachment surface 262 and the clip 270 may be mounted on a single auxiliary anchor pad 260. In addition, more than one of each may be mounted on a single auxiliary anchor pad 260. Any number of the attachment surface 262, the clip 270, and/or other means of engagement may be mounted on a single auxiliary anchor pad 260. Such means of engagement may provide multiple engagements at a time or may provide alternative areas at which to engage the medical line 54 or the auxiliary attachment surface 262. Similarly, a plurality of the auxiliary attachment surfaces 252 may be attached to the line 54 or to other medical devices farther down the line.

Any number of auxiliary anchor pads 260 may be used in the securement system 10. They may be placed on either or both sides of the anchor pad 20. In addition, each may contain one or more of the attachment surfaces 262 and the tube clips 270 or other engagement means. Any auxiliary anchor pads 260 may be spaced at any number of distances from the anchor pad 20.

Various aspects of the securement system have been described herein with reference to specific forms selected for purposes of illustration. It will be appreciated that the spirit and scope of the securement system disclosed herein is not limited to the selected forms. For example, the securement system 10 can be used to secure a retainer 320, as shown in FIG. 32. The retainer 320 is configured to engage the anchor pad 20 using the attachment surfaces 22 and 52, and configured to secure the catheter 50. The retainer 320 may be configured as described in U.S. patent application Ser. No. 12/174,537, filed Jul. 16, 2008, and entitled "SECUREMENT SYSTEM EMPLOYING POLYMERIC GEL," which is hereby incorporated by reference in its entirety.

The retainer 320 includes a body member 322 and footings/side mounting wings 324a and 324b that extend in a lateral direction from either side of the body member 322. The body member 322 defines a channel 326 that is capable of receiving a portion or length of the catheter 50 and is generally configured to house, or grip, and to secure this portion of the catheter 50. In the illustrated embodiment, the catheter 50 is shown as being secured by the retainer 320, and is also shown as being connected by a spin nut 332 to a connector fitting including an elongated body 334. The connector fitting is disposed upon the end of a medical line 336.

One or more of the attachment surfaces 52 are disposed on the underside of the retainer 320 and are configured to engage with the attachment surface 22. In the illustrated embodiment, the attachment surfaces 52 are disposed on the underside of each of the wings 324a and 324b. A plurality of the attachment surfaces 52 may be disposed on one or both of the wings 324a and 324b. When the retainer 320 is lowered onto the anchor pad 20, at least one of the attachment surfaces 52 will engage the attachment surface 22, thereby securing the retainer 320 to the anchor pad 20.

Similar to the descriptions above of FIGS. 8, 10, 16-17, and 21-13, the retainer 320 may attach to the anchor pad 20 at a plurality of locations spaced laterally and longitudinally across the anchor pad 20. The retainer 320 may also be attached to the anchor pad 20 at any orientation rotated in the plane of the anchor pad 20. Of course, the size and shape of the attachment surface 22 may be coextensive with the size and shape of the anchor pad 20, or the size and shape of the attachment surface 22 may be coextensive with either or both of the attachment surfaces 52. In addition, a plurality of attachment surfaces may be provided on the anchor pad 20 for attachment to the retainer 320. To add to this, a plurality of anchor pads, each including one or more attachment surfaces for connecting the retainer 320, may be provided.

It is to be noted that the figures provided herein are not drawn to any particular proportion or scale, and that many variations can be made to the illustrated embodiments. Those of skill in the art will recognize that the disclosed aspects and features shown herein are not limited to any particular embodiment of a securement system, and securement systems that include one or more of the features herein described can be designed for use with a variety of medical articles The various embodiments of the securement systems described above in accordance with the present invention thus provide a means to releasably secure a catheter to a patient in a plurality of positions and orientations. The catheter tube can be adjusted without removing the entire securement system, and without the need for use of additional tape to re-secure the catheter once it is properly repositioned.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Furthermore, the skilled artisan will recognize the interchangeability of various features from different embodiments. In addition to the variations described herein, other known equivalents for each feature can be mixed and matched by one of ordinary skill in this art to construct securement systems and techniques in accordance with principles of the present invention.

Although this invention has been disclosed in the context of certain embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but by a fair reading of the claims that follow.

What is claimed is:

1. A medical article assembly for securing a medical article to a patient, comprising:
   a medical article including a medical line, a connector for attachment to a fitting, and a first mounting surface with a first interlocking part, the first mounting surface comprising a body having a circular shape, the first interlocking part being disposed on the body such that the medical article can be secured in multiple rotational orientations about a longitudinal axis of the medical article, the medical line and the connector being disposed on opposite ends of the medical article; and
   a support having two opposed sides, wherein one side is configured for attachment to a patient's skin and the other side has a second mounting surface with a second interlocking part for selective engagement with the first interlocking part of the medical article so that the medical article is selectively connected to the support at any orientation and can be disconnected and repositioned at any orientation.

2. The medical article assembly of claim 1, wherein the first and second interlocking parts comprise a hook and loop fastener.

3. The medical article assembly of claim 1, wherein the support is an anchor pad and the one side configured for attachment to a patient's skin includes an adhesive surface.

4. The catheter assembly of claim 3, wherein the adhesive surface on the anchor pad is biocompatible.

5. The medical article assembly of claim 3, wherein the adhesive surface on the anchor pad is moisture vapor permeable.

6. The medical article assembly of claim 1, wherein the support includes a strap and a connector that secures the strap to the patient.

7. The medical article assembly of claim 1, wherein the first interlocking part is longitudinally aligned with the medical line.

8. The medical article assembly of claim 1, wherein the first mounting surface of the medical article comprises a cylindrical body.

9. The medical article assembly of claim 8, wherein the first interlocking part is a band adhered around the cylindrical body.

10. The medical article assembly of claim 1, wherein the first interlocking part comprises a plurality of discrete first interlocking parts.

11. The medical article assembly of claim 1, wherein the first interlocking part is adhered to the first mounting surface of the medical article.

12. The medical article assembly of claim 1, wherein the first interlocking part and the second interlocking part are substantially the same size.

13. The medical article assembly of claim 1, wherein the medical article has an auxiliary mounting surface with an auxiliary first interlocking part, and further comprising an auxiliary anchor pad with an auxiliary second interlocking part, wherein the auxiliary mounting surface is selectively mounted to the auxiliary anchor pad at any orientation.

14. The medical article assembly of claim 1, wherein the second interlocking part is configured such that the medical article may be connected to the support at a plurality of lateral locations.

15. The medical article assembly of claim 14, wherein the second interlocking part is configured such that the medical article may be connected to the support at a plurality of longitudinal locations.

16. The medical article assembly of claim 1, wherein the medical article comprises a catheter hub.

17. The medical article assembly of claim 1, wherein the first mounting surface is disposed between the medical line and the connector.

18. The medical article assembly of claim 1, wherein the connector is configured for attachment to a luer connection.

19. The medical article assembly of claim 1, wherein the medical article comprises a proximal end and a distal end, wherein the medical line is disposed at the proximal end, and wherein the connector is disposed at the distal end.

20. The medical article assembly of claim 19, wherein the connector comprises a flange.

21. The medical article assembly of claim 1, wherein the connector comprises a screw thread disposed on an external surface of the medical article.

22. A medical article assembly for securing a medical article to a patient, comprising:
a medical article comprising a medical line including a first interlocking part and a connector for attachment to a fitting, the medical article having a circular shape, the first interlocking part being disposed on the medical article such that the medical article can be secured in multiple rotational orientations about a longitudinal axis of the medical article, the medical line and the connector being disposed on opposite ends of the medical article; and
an anchor pad comprising an adhesive surface for attachment to a patient's skin, and a second interlocking part for selective engagement with the first interlocking part of the medical article so that the medical article is selectively connected to the anchor pad at any orientation in a plane generally parallel to a surface of the anchor pad.

23. The medical article assembly of claim 22, wherein the adhesive surface on the anchor pad is biocompatible.

24. The medical article assembly of claim 22, wherein the medical article comprises a cylindrical body.

25. The medical article assembly of claim 24, wherein the first interlocking part is a band secured to the cylindrical body.

26. The medical article assembly of claim 22, wherein the first interlocking part is configured such that the first interlocking part is engaged with the second interlocking part when the medical article is rotated 180 degrees about the longitudinal axis of the medical article.

27. The medical article assembly of claim 26, wherein the medical article is configured to be rolled across at least a portion of the anchor pad, the first and second interlocking parts being sized and shaped so that engagement of the first interlocking part and the second interlocking part is maintained during said rolling.

28. The medical article assembly of claim 22, wherein the medical article comprises a catheter hub.

* * * * *